(12) United States Patent
Kim et al.

(10) Patent No.: US 11,084,823 B2
(45) Date of Patent: Aug. 10, 2021

(54) SUBSTITUTED PYRROLO[2,1-F][1,2,4]TRIAZINES AS KINASE INHIBITORS

(71) Applicant: Daewoong Pharmaceutical Co., Ltd., Gyeonggi-do (KR)

(72) Inventors: In Woo Kim, Seoul (KR); Ja Kyung Yoo, Gyeonggi-do (KR); Ji Duck Kim, Gyeonggi-do (KR); Sun Ah Jun, Gyeonggi-do (KR); Jun Hee Lee, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 103 days.

(21) Appl. No.: 16/478,920

(22) PCT Filed: Mar. 19, 2018

(86) PCT No.: PCT/KR2018/003140
§ 371 (c)(1),
(2) Date: Jul. 18, 2019

(87) PCT Pub. No.: WO2018/169373
PCT Pub. Date: Sep. 20, 2018

(65) Prior Publication Data
US 2021/0130358 A1    May 6, 2021

(30) Foreign Application Priority Data
Mar. 17, 2017 (KR) .................. 10-2017-0034059

(51) Int. Cl.
*A61K 31/519* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ..................... A61K 31/519; C07D 487/04
USPC ....................... 514/259.1; 544/281
See application file for complete search history.

(56) References Cited

U.S. PATENT DOCUMENTS

| | | |
|---|---|---|
| 2006/0009454 A1 | 1/2006 | Cai et al. |
| 2010/0063038 A1 | 3/2010 | Dixon et al. |
| 2010/0179125 A1 | 7/2010 | Dixon et al. |
| 2015/0336982 A1 | 11/2015 | Xu et al. |
| 2016/0046627 A1 | 2/2016 | Vankayalapati et al. |
| 2016/0229865 A1 | 8/2016 | Liu et al. |
| 2017/0128439 A1 | 5/2017 | Liu et al. |
| 2018/0051036 A1 | 2/2018 | Liu et al. |

FOREIGN PATENT DOCUMENTS

| | | |
|---|---|---|
| CN | 101379065 A | 3/2009 |
| CN | 101466710 A | 6/2009 |
| CN | 103936757 A | 7/2014 |
| CN | 104829610 A | 8/2015 |
| CN | 104974163 A | 10/2015 |
| CN | 105646497 A | 6/2016 |
| CN | 10-5837572 A | 8/2016 |
| CN | 106432249 A | 2/2017 |
| JP | 2016-516823 A | 6/2016 |
| JP | 2016-530335 | 9/2016 |
| RU | 2331640 C2 | 8/2008 |
| WO | WO-2000/71129 A1 | 11/2000 |
| WO | WO-2002/096909 A1 | 12/2002 |
| WO | WO-2009/062258 A1 | 5/2009 |
| WO | WO-2010/009342 A2 | 1/2010 |
| WO | WO-2011/079231 A1 | 6/2011 |
| WO | WO-2011/140488 A1 | 11/2011 |
| WO | WO-2013/042006 A1 | 3/2013 |
| WO | WO-2015/039612 A1 | 3/2015 |

OTHER PUBLICATIONS

Extended European Search Report in EP Application No. 18766994.0 dated Oct. 19, 2020, 14 pages.
Office Action in JP Application No. 2019-571195 dated Oct. 6, 2020, 4 pages.
Swanson et al., "Tyrosine Kinases as Targets for the Treatment of Rheumatoid Arthritis", Nature Reviews Rheumatology, vol. 5, Jun. 2009, pp. 317-324.
Peter Norman, "Selective JAK Inhibitors in Development for Rheumatoid Arthritis", Expert Opin. Investig. Drugs, 23(8), Aug. 2014, 11 pages.
Whang et al., "Bruton's Tyrosine Kinase Inhibitors for the Treatment of Rheumatoid Arthritis", Drug Discov. Today, 19(8), Aug. 2014, 8 pages.
Search Report and Written Opinion in International Application No. PCT/KR2018/003140 dated Jul. 24, 2018, 10 pages.
(Continued)

*Primary Examiner* — Douglas M Willis
(74) *Attorney, Agent, or Firm* — Marshall, Gerstein & Borun LLP

(57) ABSTRACT

The present invention relates to a compound represented by the Chemical Formula 1 defined in the present specification, or a pharmaceutically acceptable salt thereof. The compound according to the present invention can be usefully used for the prevention or treatment of diseases which are associated with kinase inhibitory actions.

[Chemical Formula 1]

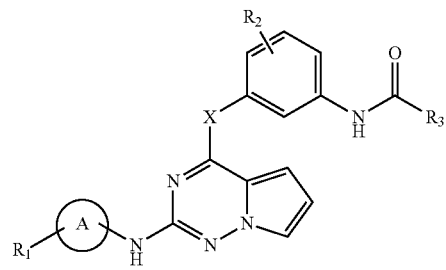

9 Claims, No Drawings

(56) References Cited

OTHER PUBLICATIONS

Office Action in RU Application No. 2019123998 dated Jan. 13, 2020, 15 pages.
First Office Action in CN Application No. 201880006529.0 dated Apr. 30, 2021, 11 pages.

SUBSTITUTED PYRROLO[2,1-F][1,2,4]TRIAZINES AS KINASE INHIBITORS

TECHNICAL FIELD

The present relates to a pyrrolotriazine derivative having kinase inhibitory activity, a process for preparing the same and use thereof.

BACKGROUND OF ART

Protein kinase is an enzyme that catalyzes phosphorylation of specific residues of other proteins, and plays an important role in signal-transduction pathways that transduce extracellular signals to the nucleus. Further, it is involved in various diseases in vivo. In the onset or development of inflammatory disease, autoimmune disease, proliferative disease or hyperproliferative disease, and/or immunity mediated disease, there is various evidence that T-cells (or T-lymphocytes) and B-cells (or B-lymphocytes) play an important role.

Janus kinase (hereinafter referred to as "JAK") is a cytoplasmic protein tyrosine kinase that plays pivotal roles in regulating cell function in the lympho-hematopoietic system. Cytokines are known to play an important role in regulating inflammation, immunity and normal cell function, and JAK activates STAT (Signal Transducer and Activators of Transcription) proteins through tyrosine phosphorylation to provide rapid signaling pathways to cytokines. JAK/STAT signaling is known to be associated with allergies, asthma, autoimmune diseases (e.g., transplant rejection, rheumatoid arthritis, amyotrophic lateral sclerosis, multiple sclerosis etc.), solid cancers, blood cancers (e.g., leukemia, lymphoma and so on).

The JAK family is classified into four members: JAK 1, JAK 2, JAK 3, and TYK 2. Members of the JAK family pair with each other to mediate signals from a variety of cytokines. It includes JAK2 and JAK1 associated with hematopoietic growth factor signaling, and a combination of TYK2 and AK2 is important for interferon signaling and contributes to host tolerance. JAK2 can induce anemia, thrombocytopenia, leukopenia, especially when it is involved in the hematopoietic growth factor signaling and causes excessive inhibition.

The expression of JAK1, JAK2, and TYK2 was found to be widely distributed, whereas the expression of JAK3 was restricted to lymphocytes and is associated with signaling for the common gamma chains, members of IL-2, IL-4, IL-7, IL-9, IL-15 and IL-21 receptors, particularly the common gamma chain of the IL-2 family. As soon as the cytokine is bound, the receptor carries adjacent JAK3 nearby, which induces autophosphorylation of the β-chain C-terminus. As a result, it causes activation of the STAT protein, which is an important step in retransmitting the signal to the nucleus. JAK3 controls the signal pathways of various cytokines through this process. This makes JAK3 as an attractive target for immunosuppression.

B cells play an important role in the development of autoimmune and/or inflammatory diseases. Protein-based therapeutic agents that reduce B cells, for example Rituxan, are effective in autoantibody-induced inflammatory diseases such as rheumatoid arthritis. Thus, protein kinase inhibitors that play a role in B cell activation are useful therapeutic agents for the treatment of B cell-mediated diseases, for example, for the production of autoantibodies.

Signal transduction through B cell receptor (BCR) regulates various B cell responses, including proliferation and differentiation into mature antibody-producing cells. BCR is an important regulatory element of B cell activity, and abnormal signal transduction can cause the formation of pathogenic autoantibodies leading to a plurality of autoimmune and/or inflammatory diseases and the proliferation of deregulated B cell.

Bruton's tyrosine kinase (hereinafter, referred to as "BTK") is an important regulator of the development, activation, signaling and survival of B-cells. BTK is involved in signal transduction pathways initiated by binding various extracellular ligands to their cell surface receptors. Following ligation of the B cell antigen receptor (BCR), the activity of BTK by the coincident action of the protein tyrosine kinases Lyn and Syk is required for the induction of the phospholipase C-γ2-mediated calcium mobilization. Therefore, inhibition of BTK can be a useful therapeutic approach in blocking the onset process of B-cell mediated diseases.

As mentioned above, Janus kinase and TEC-based kinases plays an important role in the activation of T-cells and/or B-cells involved in the development of inflammatory diseases, autoimmune diseases, proliferative diseases or hyperproliferative diseases, and immunity mediated diseases. Therefore, the development of substances that effectively inhibit these diseases can be useful as a related therapeutic agent. Specific examples of the diseases which can be treated and prevented include cancer, transplant rejection, multiple sclerosis, rheumatoid arthritis, psoriatic arthritis, psoriasis, asthma, allergic dermatitis, atopic dermatitis, eczema, type I diabetes, diabetic complication, ulcerative colitis, Crohn's disease, autoimmune thyroid disorder, systemic depilation, Sjogren's syndrome and the like.

JAK3 kinase inhibitor, tofacitinib (CP-690550) (Pfizer Inc.) is currently approved and marketed for the treatment of rheumatoid arthritis. In addition, a BTK kinase inhibitor, ibrutinib (PCI-32765) (Pharmacyclics) is in a clinical stage, but severe side effects such as skin rash and diarrhea have been reported in clinical cases. Thus, there is a need to develop a more stable and effective substance that inhibits JAK and/or BTK (see, Nat Rev Rheumatol. 2009 Jun. 5(6) 317-24; Expert Opin Investig Drugs. 2014 Aug. 23(8) 1067-77; Drug Discov Today 2014 Aug. 19(8) 1200-4; WO2002/096909; WO2010-009342).

Therefore, the present inventors have found a new pyrrolotriazine derivative having an excellent inhibitory activity as a kinase inhibitor, thereby completing the present invention.

DETAILED DESCRIPTION OF THE INVENTION

Technical Problem

It is one object of the present invention to provide a new pyrrolotriazine derivative having kinase inhibitory activity, and a process for preparing the same.

It is another object of the present invention to provide a pharmaceutical composition comprising the pyrrolotriazine derivative as an active ingredient.

Technical Solution

In order to achieve the above objects, the present invention provides a compound represented by the following Chemical Formula 1, or a pharmaceutically acceptable salt thereof:

[Chemical Formula 1]

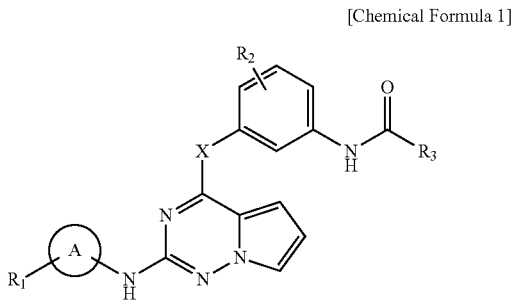

in Chemical Formula 1,

X is O, or NH,

A is a divalent $C_{6-10}$ aromatic ring, or a divalent $C_{2-10}$ heteroaromatic ring containing one to three heteroatoms each independently selected from the group consisting of N, O and S, $R_1$ is hydrogen; $C_{1-4}$ alkyl unsubstituted or substituted with one substituent selected from the group consisting of $C_{1-4}$ alkoxy, $N(C_{1-4}$ alkyl$)_2$, cyano, and $(C_{1-4}$ alkyl)-NHCO; $C_{1-4}$ alkoxy; $C_{1-4}$ haloalkyl; $C_{3-6}$ cycloalkyl; $N(C_{1-4}$ alkyl$)_2$; benzoyl; pyrazolyl unsubstituted or substituted with one or two $C_{1-4}$ alkyl; or

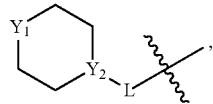

wherein $Y_1$ is NH, $N(C_{1-4}$ alkyl), or O; $Y_2$ is CH or N; L is a bond, $C_{1-4}$ alkylene, or CO, $R_2$ is hydrogen, $C_{1-4}$ alkyl, or halogen, and $R_3$ is $C_{1-4}$ alkyl substituted by halogen or cyano; $C_{2-4}$ alkenyl unsubstituted or substituted with halogen; or $C_{2-4}$ alkynyl.

Preferably, A is a divalent ring selected from the group consisting of benzene, benzothiazole, isothiazole, isoxazole, pyrazole, pyridine, pyrrole, thiazole, thiophene, and 4,5,6,7-tetrahydropyrazolo [1,5-a]pyrazine.

Preferably, $R_1$ is hydrogen, methyl, ethyl, propyl, isopropyl, butyl, isobutyl, methoxyethyl, dimethylaminomethyl, diethylaminoethyl, cyanomethyl, methylaminocarbonylmethyl, methoxy, difluoromethyl, 2,2-difluoroethyl, 2,2,2-trifluoroethyl, cyclopropyl, dimethylamino, benzoyl, or 3,5-dimethyl-1H-pyrazol-1-yl.

Preferably, $R_1$ is piperidin-4-yl, 1-methyl-piperidin-4-yl, 4-methylpiperazin-1-yl, tetrahydro-2H-pyran-4-yl, morpholino, 2-morpholinoethyl, or morpholine-4-carbonyl.

Preferably, $R_2$ is hydrogen, methyl, chloro, or fluoro.

Preferably, $R_3$ is —$CH_2$—Cl, —CH=$CH_2$, —CH=CHCH$_2$CH$_3$, —CH=CHCH$_2$Cl, or —C≡CCH$_2$CH$_3$.

Typical examples of the compounds represented by Chemical Formula 1 are as follows:

1) N-(3-((2-((1-cyclopropyl-1H-pyrazol-4-yl)amino)pyrrolo[2,1-f][1,2,4]triazin-4-yl)oxy)-4-fluorophenyl)acrylamide,
2) N-(3-((2-((4-(4-methylpiperazin-1-yl)phenyl)amino)pyrrolo[2,1-f][1,2,4]triazin-4-yl)oxy)phenyl)acrylamide,
3) N-(3-((2-((1-methyl-1H-pyrazol-4-yl)amino)pyrrolo[2,1-f][1,2,4]triazin-4-yl)oxy)phenyl)acrylamide,
4) N-(3-((2-((1-(2,2-difluoroethyl)-1H-pyrazol-4-yl)amino)pyrrolo[2,1-f][1,2,4]triazin-4-yl)oxy)phenyl)acrylamide,
5) N-(3-((2-((3-methylisothiazol-5-yl)amino)pyrrolo[2,1-f][1,2,4]triazin-4-yl)oxy)phenyl)acrylamide,
6) N-(3-((2-((1-ethyl-1H-pyrazol-4-yl)amino)pyrrolo[2,1-f][1,2,4]triazin-4-yl)oxy)phenyl)acrylamide,
7) N-(4-fluoro-3-((2-((3-methylisothiazol-5-yl)amino)pyrrolo[2,1-f][1,2,4]triazin-4-yl)oxy)phenyl)acrylamide,
8) N-(3-((2-((1-ethyl-1H-pyrazol-4-yl)amino)pyrrolo[2,1-f][1,2,4]triazin-4-yl)oxy)-4-fluorophenyl)acrylamide,
9) N-(4-fluoro-3-((2-((1-methyl-1H-pyrrol-3-yl)amino)pyrrolo[2,1-f][1,2,4]triazin-4-yl)oxy)phenyl)acrylamide,
10) N-(4-fluoro-3-((2-((1-isobutyl-1H-pyrazol-4-yl)amino)pyrrolo[2,1-f][1,2,4]triazin-4-yl)oxy)phenyl)acrylamide,
11) N-(3-((2-((1-cyclopropyl-1H-pyrazol-4-yl)amino)pyrrolo[2,1-f][1,2,4]triazin-4-yl)oxy)phenyl)acrylamide,
12) N-(3-((2-((4-(dimethylamino)phenyl)amino)pyrrolo[2,1-f][1,2,4]triazin-4-yl)oxy)-4-fluorophenyl)acrylamide,
13) N-(4-fluoro-3-((2-((4-phenoxyphenyl)amino)pyrrolo[2,1-f][1,2,4]triazin-4-yl)oxy)phenyl)acrylamide,
14) N-(3-((2-((benzo[d]thiazol-6-yl)amino)pyrrolo[2,1-f][1,2,4]triazin-4-yl)oxy)-4-fluorophenyl)acrylamide,
15) N-(4-fluoro-3-((2-((pyridin-3-yl)amino)pyrrolo[2,1-f][1,2,4]triazin-4-yl)oxy)phenyl)acrylamide,
16) N-(3-((2-((4-isopropylphenyl)amino)pyrrolo[2,1-f][1,2,4]triazin-4-yl)oxy)phenyl)acrylamide,
17) N-(3-((2-((4-methoxyphenyl)amino)pyrrolo[2,1-f][1,2,4]triazin-4-yl)oxy)phenyl)acrylamide,
18) N-(3-((2-((4-(morpholine-4-carbonyl)phenyl)amino)pyrrolo[2,1-f][1,2,4]triazin-4-yl)oxy)phenyl)acrylamide,
19) N-(3-((2-((thiophen-3-yl)amino)pyrrolo[2,1-f][1,2,4]triazin-4-yl)oxy)phenyl)acrylamide,
20) N-(3-((2-((1-methyl-1H-pyrazol-3-yl)amino)pyrrolo[2,1-f][1,2,4]triazin-4-yl)oxy)phenyl)acrylamide,
21) N-(3-((2-((4-((dimethylamino)methyl)phenyl)amino)pyrrolo[2,1-f][1,2,4]triazin-4-yl)oxy)phenyl)acrylamide,
22) N-(3-((2-((4-morpholinophenyl)amino)pyrrolo[2,1-f][1,2,4]triazin-4-yl)oxy)phenyl)acrylamide,
23) N-(3-((2-((4-(dimethylamino)phenyl)amino)pyrrolo[2,1-f][1,2,4]triazin-4-yl)oxy)phenyl)acrylamide,
24) N-(3-((2-((5-methyl-4,5,6,7-tetrahydropyrazolo[1,5-a]pyrazin-2-yl)amino)pyrrolo[2,1-f][1,2,4]triazin-4-yl)oxy)phenyl)acrylamide,
25) N-(4-fluoro-3-((2-((4-(4-methylpiperazin-1-yl)phenyl)amino)pyrrolo[2,1-f][1,2,4]triazin-4-yl)oxy)phenyl)acrylamide,
26) N-(3-((2-((1-(2,2-difluoroethyl)-1H-pyrazol-4-yl)amino)pyrrolo[2,1-f][1,2,4]triazin-4-yl)oxy)-4-fluorophenyl)acrylamide,
27) N-(4-fluoro-3-((2-((1-methyl-1H-pyrazol-4-yl)amino)pyrrolo[2,1-f][1,2,4]triazin-4-yl)oxy)phenyl)acrylamide,
28) N-(4-fluoro-3-((2-((4-methoxyphenyl)amino)pyrrolo[2,1-f][1,2,4]triazin-4-yl)oxy)phenyl)acrylamide,
29) N-(4-fluoro-3-((2-((4-(morpholine-4-carbonyl)phenyl)amino)pyrrolo[2,1-f][1,2,4]triazin-4-yl)oxy)phenyl)acrylamide,
30) N-(4-fluoro-3-((2-((thiophen-3-yl)amino)pyrrolo[2,1-f][1,2,4]triazin-4-yl)oxy)phenyl)acrylamide,
31) N-(4-fluoro-3-((2-((4-morpholinophenyl)amino)pyrrolo[2,1-f][1,2,4]triazin-4-yl)oxy)phenyl)acrylamide,
32) N-(4-fluoro-3-((2-((1-propyl-1H-pyrazol-4-yl)amino)pyrrolo[2,1-f][1,2,4]triazin-4-yl)oxy)phenyl)acrylamide,
33) N-(3-((2-((1-(difluoromethyl)-1H-pyrazol-4-yl)amino)pyrrolo[2,1-f][1,2,4]triazin-4-yl)oxy)-4-fluorophenyl)acrylamide, 34) N-(4-fluoro-3-((2-((1-(tetrahydro-2H-pyran-4-yl)-1H-pyrazol-4-yl)amino)pyrrolo[2,1-f][1,2,4]triazin-4-yl)oxy)phenyl)acrylamide,
35) N-(4-fluoro-3-((2-((1-(2-morpholinoethyl)-1H-pyrazol-4-yl)amino)pyrrolo[2,1-f][1,2,4]triazin-4-yl)oxy)phenyl)acrylamide,
36) N-(4-fluoro-3-((2-((1-isopropyl-1H-pyrazol-4-yl)amino)pyrrolo[2,1-f][1,2,4]triazin-4-yl)oxy)phenyl)acrylamide,
37) N-(4-fluoro-3-((2-((1-(piperidin-4-yl)-1H-pyrazol-4-yl)amino)pyrrolo[2,1-f][1,2,4]triazin-4-yl)oxy)phenyl)acrylamide,
38) N-(4-fluoro-3-((2-((1-(2,2,2-trifluoroethyl)-1H-pyrazol-4-yl)amino)pyrrolo[2,1-f][1,2,4]triazin-4-yl)oxy)phenyl)acrylamide,
39) N-(3-((2-((4-(3,5-dimethyl-1H-pyrazol-1-yl)phenyl)amino)pyrrolo[2,1-f][1,2,4]triazin-4-yl)oxy)-4-fluorophenyl)acrylamide,
40) N-(4-fluoro-3-((2-((1-(2-methoxyethyl)-1H-pyrazol-4-yl)amino)pyrrolo[2,1-f][1,2,4]triazin-4-yl)oxy)phenyl)acrylamide,
41) 2-chloro-N-(3-((2-((1-(2,2-difluoroethyl)-1H-pyrazol-4-yl)amino)pyrrolo[2,1-f][1,2,4]triazin-4-yl)oxy)-4-fluorophenyl)acetamide,
42) 2-chloro-N-(4-fluoro-3-((2-((1-(tetrahydro-2H-pyran-4-yl)-1H-pyrazol-4-yl)amino)pyrrolo[2,1-f][1,2,4]triazin-4-yl)oxy)phenyl)acetamide,
43) 2-chloro-N-(3-((2-((1-ethyl-1H-pyrazol-4-yl)amino)pyrrolo[2,1-f][1,2,4]triazin-4-yl)oxy)-4-fluorophenyl)acetamide,
44) (E)-4-chloro-N-(3-((2-((1-ethyl-1H-pyrazol-4-yl)amino)pyrrolo[2,1-f][1,2,4]triazin-4-yl)oxy)-4-fluorophenyl)but-2-enamide,
45) N-(4-fluoro-3-(2-(isoxazol-4-ylamino)pyrrolo[2,1-f][1,2,4]triazin-4-yloxy)phenyl)acrylamide,
46) N-(4-chloro-3-((2-((1-ethyl-1H-pyrazol-4-yl)amino)pyrrolo[2,1-f][1,2,4]triazin-4-yl)oxy)phenyl)acrylamide,
47) N-(5-((2-((1-ethyl-1H-pyrazol-4-yl)amino)pyrrolo[2,1-f][1,2,4]triazin-4-yl)oxy)-2-methylphenyl)acrylamide,
48) N-(5-((2-((1-(2,2-difluoroethyl)-1H-pyrazol-4-yl)amino)pyrrolo[2,1-f][1,2,4]triazin-4-yl)oxy)-2-methylphenyl)acrylamide, and
49) N-(3-((2-((1-(2,2-difluoroethyl)-1H-pyrazol-4-yl)amino)pyrrolo[2,1-f][1,2,4]triazin-4-yl)oxy)-4-fluorophenyl)pent-2-ynamide.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

Pharmaceutically acceptable salts can be obtained by conventional methods using inorganic or organic acids. For example, the pharmaceutically acceptable salt can be prepared by dissolving the compound represented by Chemical Formula 1 in a water-miscible organic solvent, e.g., acetone, methanol, ethanol or acetonitrile, followed by adding an organic acid or an inorganic acid, and filtering and drying the precipitated crystals. Alternatively, it may be prepared by subjecting a solvent or an excessive amount of acid from the acid-added reaction mixture to reduced pressure and then drying the residue, or by adding a different organic solvent and then filtering the precipitated salt. At this time, the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid or toluenesulfonic acid, and the like.

A pharmaceutically unacceptable salt or solvate of the compound of Chemical Formula 1 may be used as an intermediate in the production of the compound of Chemical Formula 1, or the pharmaceutically acceptable salt or the solvate thereof.

The compound of Chemical Formula 1 according to the present invention includes not only pharmaceutically acceptable salts thereof, but all solvates and hydrates that can be prepared therefrom, and includes all possible stereoisomers as well. The solvate, the hydrate and the stereoisomer of the compound represented by Chemical Formula 1 may be prepared and used from the compound of Chemical Formula 1 using common methods.

In addition, the compound represented by Chemical Formula 1 according to the present invention may be prepared either in a crystalline form or in a non-crystalline form, and when the compound represented by Chemical Formula 1 is prepared in a crystalline form, it may be optionally hydrated or solvated. In the present invention, the compound represented by Chemical Formula 1 may not only include a stoichiometric hydrate, but include a compound containing various amounts of water. The solvate of the compound represented by Chemical Formula 1 according to the present invention includes both stoichiometric solvates and non-stoichiometric solvates.

Furthermore, as an example, the present invention can produce the compound represented by Chemical Formula 1 through Reaction Scheme 1 below.

[Reaction Scheme 1]

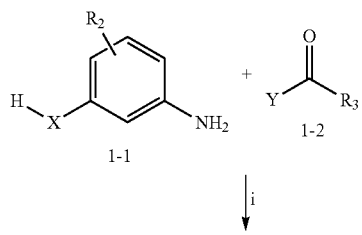

-continued

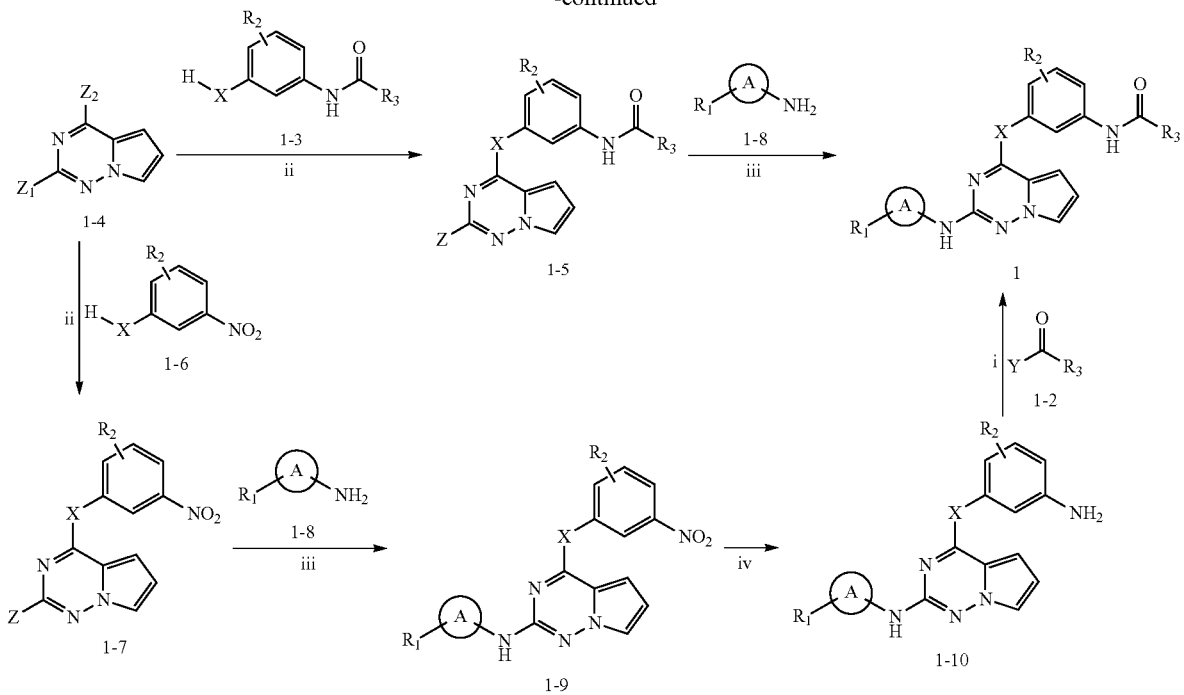

(in Reaction Scheme 1, X, A and $R_1$ to $R_3$ are as previously defined, $Z_1$ and $Z_2$ are each independently halogen, and Y is halogen, or OH)

Step i is a step of preparing a compound represented by Chemical Formula 1-3 or Chemical Formula 1 by reacting a compound represented by Chemical Formula 1-1 or 1-10 with a compound (Y=Cl) represented by Chemical Formula 1-2. The reaction is preferably carried out under the conditions of triethylamine or sodium hydrogencarbonate. The reaction temperature is preferably −20° C. to 0° C., and the reaction time is preferably 30 minutes to 24 hours. The solvent for the reaction is preferably a mixed solution of dichloromethane or tetrahydrofuran and water.

Alternatively, Step i can be carried out by reacting Y=OH instead of Y=Cl in Chemical Formula 1-2. In this case, the reaction is preferably carried out under the conditions of diisopropylethylamine, O-(7-azabenzotriazol-1-yl)-N,N,N',N'-tetramethylruronium hexafluorophosphate (O-HATU) at room temperature for 24 hours, and the solvent for the reaction is preferably tetrahydrofuran, dimethylformamide, or dimethylsulfoxide.

Step ii is a step of preparing a compound represented by Chemical Formula 1-5 or 1-7 by reacting a compound represented by Chemical Formula 1-4 with a compound represented by Chemical Formula 1-3 or 1-6. The reaction is preferably carried out in the presence of a base. In addition, the reaction temperature is preferably room temperature or 40 to 60° C. Further, the reaction time is preferably 1 hour to 6 hours. The solvent for the reaction is preferably dimethylformamide, 1,4-dioxane, dimethylsulfoxide, or toluene. Further, the base is preferably potassium carbonate, cesium carbonate, diisopropylamine, or sodium hydride.

Step iii is a step of preparing a compound represented by Chemical Formula 1 or 1-9 by reacting a compound represented by Chemical Formula 1-5 or 1-7 with a compound represented by Chemical Formula 1-8. The reaction can be carried out in the presence of a base such as tris(dibenzylideneacetone)dipalladium ($Pd_2(dba)_3$), palladium acetate (Pd$(OAc)_2$), or [1,1'-bis(diphenylphosphine)ferrocene]palladium dichloride ((Pd(Dppf)$Cl_2$) under basic conditions. The reaction temperature is preferably 50° C. to 150° C. In addition, the reaction solvent is preferably 1,4-dioxane, toluene, t-butanol or dimethylformamide. Further, the base is preferably an inorganic alkali such as cesium carbonate, calcium carbonate, sodium carbonate, potassium phosphate or the like.

Step iv is a step of preparing a compound represented by Chemical Formula 1-10 by reducing the compound represented by Chemical Formula 1-9. The reaction is preferably carried out in a mixture of ammonium chloride, 1,4-dioxane and water in the presence of tin. In addition, the reaction temperature is preferably 0° C. to room temperature. Further, the reaction time is preferably 30 minutes to 3 hours. Further, the reaction can be carried out by using methanol in the presence of 10% palladium/carbon or by using metal (iron) or metal salt (stannous chloride) in hydrochloric acid or ethanol.

Further, the present invention provides a pharmaceutical composition for preventing or treating diseases which is beneficial for kinase inhibitory actions, comprising the compound represented by Chemical Formula 1, or a pharmaceutically acceptable salt, hydrate, solvate or isomer thereof as an active ingredient.

In this case, the diseases which are associated with kinase inhibitory actions includes inflammatory diseases, autoimmune diseases, proliferative diseases or hyperproliferative diseases, and immunity mediated diseases, cancers, tumors or the like.

The term "prevention" as used herein refers to any act to delay or inhibit occurrence, spread or recurrence of the above-mentioned diseases by administration of the composition of the present invention, and the term "treatment" as used herein refers to any act to improve or change the symptoms of the above diseases for the better by administration of the composition of the present invention.

The pharmaceutical composition of the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

Pharmaceutical dosage forms of the compounds of the present invention may include using the compounds in the form of pharmaceutically acceptable salts or solvates thereof, and using the compounds alone or as a combination and/or a suitable mixture together with other pharmaceutically active compounds.

The compounds of the present invention can be formulated into injection solutions by dissolving, suspending or emulsifying the compounds in a water-soluble solvent such as normal saline, 5% dextrose or a non-aqueous solvent such as synthetic fatty acid glyceride, higher fatty acid ester or propylene glycol. Formulations of the present invention may include conventional additives such as solubilizers, isotonic agents, suspending agents, emulsifying agents, stabilizers and preservatives.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administered daily at a dose of 0.0001 to 100 mg/kg (body weight), and preferably 0.001 to 100 mg/kg (body weight). The administration may be performed once a day or in divided doses each day through an oral or parenteral route. Depending on the method of administration, the composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof can be usefully used for the prevention or treatment of diseases which are associated with kinase inhibitory actions.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1

Preparation of N-(3-((2-((1-cyclopropyl-1H-pyrazol-4-yl)amino)pyrrolo[2,1-f][1,2,4]triazin-4-yl)oxy)-4-fluorophenyl)acrylamide

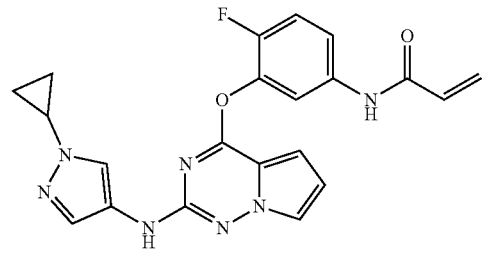 [SMILES: C=CC(=O)Nc1ccc(F)c(Oc2nc(Nc3cnn(C4CC4)c3)nn3cccc23)c1]

Step 1) Preparation of N-(4-fluoro-3-hydroxyphenyl)acrylamide

After 5-amino-2-fluorophenol (1,000.0 mg, 1.0 eq) and sodium bicarbonate (712.0 mg, 1.5 eq) were dissolved in THF/distilled water (15.0 mL/3.0 mL), acryloyl chloride (712.0 mg, 1.0 eq) was added thereto. After the reaction solution was stirred at room temperature for 24 hours, the reaction was terminated. Extraction was performed by adding dichloromethane and then adding an ammonium chloride aqueous solution. Then, the extracts were dried over anhydrous sodium sulfate, and concentrated under reduced pressure. The resulting residue was purified by column chromatography (ethyl acetate:hexane=1:1) to obtain N-(4-fluoro-3-hydroxyphenyl) acrylamide (1,135.0 mg, 79.6%).

$^1$H NMR (500 MHz, CD$_3$OD) δ 7.40-7.39 (m, 1H), 6.99-6.98 (m, 2H), 6.44-6.33 (m, 2H), 5.77-5.75 (m, 1H)

Step 2) Preparation of N-(3-((2-chloropyrrolo[2,1-f][1,2,4]triazin-4-yl)oxy)-4-fluorophenyl)acrylamide After N-(4-fluoro-3-hydroxyphenyl)acrylamide (505.9 mg, 1.1 eq) and 2,4-dichloropyrrolo[2,1-f][1,2,4]triazine (500.0 mg, 1.0 eq) were dissolved in N,N-dimethylformamide (10.0 mL), K$_2$CO$_3$ (385.9 mg, 1.1 eq) was added thereto. The reaction solution was stirred at 50° C. for 2 hours, and then cooled to room temperature. Extraction was carried out by adding dichloromethane and then adding distilled water. Then, the extracts was dried over anhydrous sodium sulfate, and concentrated under reduced pressure. The resulting residue was purified by column chromatography (ethyl acetate:hexane=1:1) to obtain N-(3-((2-chloropyrrolo[2,1-f][1,2,4]triazin-4-yl)oxy)-4-fluorophenyl)acrylamide 640.0 mg, 72.3%).

$^1$H NMR (500 MHz, CD$_3$OD) δ 7.92-7.91 (m, 1H), 7.85-7.83 (m, 1H), 7.56-7.52 (m, 1H), 7.29 (t, 1H), 7.14-7.13 (m, 1H), 6.96-6.95 (m, 1H), 6.44-6.34 (m, 2H), 5.79 (dd, 1H)

Step 3) Preparation of N-(3-((2-((1-cyclopropyl-1H-pyrazol-4-yl)amino)pyrrolo[2,1-f][1,2,4]triazin-4-yl)oxy)-4-fluorophenyl)acrylamide After N-(3-((2-chloropyrrolo[2,1-f][1,2,4]triazin-4-yl)oxy)-4-fluorophenyl)acrylamide (30.0 mg, 1.0 eq.) and 1-cyclopropyl-1H-pyrazol-4-amine (11.1 mg, 1.0 eq) were dissolved in 1.0 mL of 1,4-dioxane. After adding Pd(OAc)$_2$ (1.0 mg, 0.05 eq), Xanthphos (5.2 mg, 0.1 eq) and Cs$_2$CO$_3$ (58.6 mg, 2.0 eq), N$_2$ gas purge was done for 30 minutes. The reaction solution was reacted using a microwave (150° C., 30 minutes, normal). The reaction solution was filtered, and the filtrate was concentrated under reduced pressure. The obtained concentrated residue was purified by column chromatography (ethyl acetate:hexane=1:1) to obtain N-(3-((2-((1-cyclopropyl-1H-pyrazol-4-yl)amino)pyrrolo[2,1-f][1,2,4]triazin-4-yl)oxy)-4-fluorophenyl)acrylamide (3.5 mg, 9.3%).

$^1$H NMR (500 MHz, CD$_3$OD) δ 7.80-7.78 (m, 2H), 7.66-7.65 (m, 1H), 7.58-7.55 (m, 1H), 7.37 (s, 1H), 7.27 (t, 1H), 6.89 (dd, 1H), 6.66 (dd, 1H), 6.44-6.34 (m, 2H), 5.79 (dd, 1H), 3.53-3.50 (m, 1H), 1.00-0.99 (m, 4H)

Comparative Example 2

Preparation of N-(3-((2-((4-(4-methylpiperazin-1-yl)phenyl)amino)pyrrolo[2,1-f][1,2,4]triazin-4-yl)oxy)phenyl)acrylamide

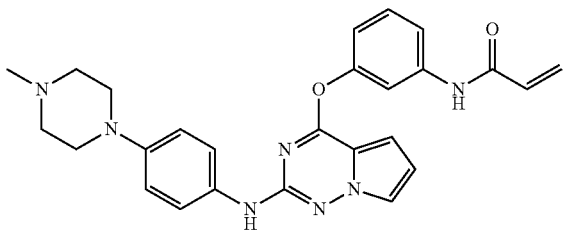 [SMILES: C=CC(=O)Nc1cccc(Oc2nc(Nc3ccc(N4CCN(C)CC4)cc3)nn3cccc23)c1]

A title compound (12.8 mg, yield: 28.6%) was obtained in the same manner as in Example 1, except that 4-(4-methylpiperazin-1-yl)aniline was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.70 (s, 1H), 7.58 (s, 1H), 7.56-7.54 (m, 1H), 7.47-7.45 (m, 2H), 7.43-7.40 (m, 1H), 7.04-7.03 (m, 1H), 6.90-6.86 (m, 2H), 6.84-6.83 (m, 1H), 6.62-6.61 (m, 1H), 6.46-6.35 (m, 2H), 5.79-5.77 (m, 1H), 3.11-3.09 (m, 4H), 2.64-2.62 (m, 4H), 2.35 (s, 3H)

Example 3

Preparation of N-(3-((2-((1-methyl-1H-pyrazol-4-yl)amino)pyrrolo[2,1-f][1,2,4]triazin-4-yl)oxy)phenyl)acrylamide

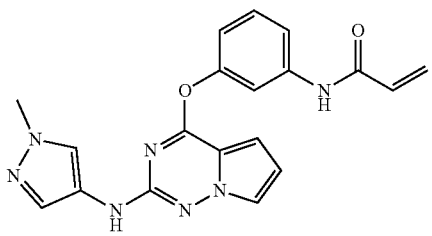 [SMILES: C=CC(=O)Nc1cccc(Oc2nc(Nc3cnn(C)c3)nn3cccc23)c1]

A title compound (3.7 mg, yield: 10.3%) was obtained in the same manner as in Example 1, except that 1-methyl-1H-pyrazol-4-amine was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.74 (br s, 1H), 7.69 (s, 1H), 7.61 (s, 1H), 7.56-7.54 (m, 1H), 7.43 (t, 1H), 7.36 (s, 1H), 7.04-7.02 (m, 1H), 6.85-6.84 (m, 1H), 6.63-6.62 (m, 1H), 6.45-6.34 (m, 2H), 5.79-5.77 (m, 1H), 3.79 (s, 3H)

Example 4

Preparation of N-(3-((2-((1-(2,2-difluoroethyl)-1H-pyrazol-4-yl)amino)pyrrolo[2,1-f][1,2,4]triazin-4-yl)oxy)phenyl)acrylamide

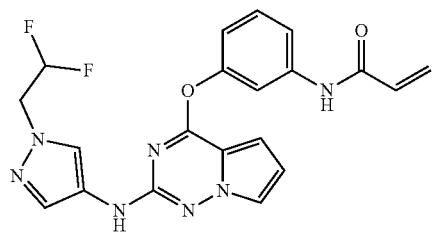 [SMILES: C=CC(=O)Nc1cccc(Oc2nc(Nc3cnn(CC(F)F)c3)nn3cccc23)c1]

A title compound (4.1 mg, yield: 10.1%) was obtained in the same manner as in Example 1, except that 1-(2,2-difluoroethyl)-1H-pyrazol-4-amine was used instead of 1-cyclopropyl-1H-pyrazol-4-amine, and 5-amino-phenol was used instead of instead of 5-amino-2-fluorophenol in Example 1.

$^1$H NMR (500 MHz, CD$_3$OD) δ 7.88 (br s, 1H), 7.70 (s, 1H), 7.63 (s, 1H), 7.56-7.54 (m, 1H), 7.45-7.41 (m, 2H), 7.05-7.03 (m, 1H), 6.86-6.85 (m, 1H), 6.64-6.63 (m, 1H), 6.45-6.34 (m, 2H), 6.21-5.98 (m, 1H), 5.78 (dd, 1H), 4.43 (td, 2H)

Example 5

Preparation of N-(3-((2-((3-methylisothiazol-5-yl)amino)pyrrolo[2,1-f][1,2,4]triazin-4-yl)oxy)phenyl)acrylamide

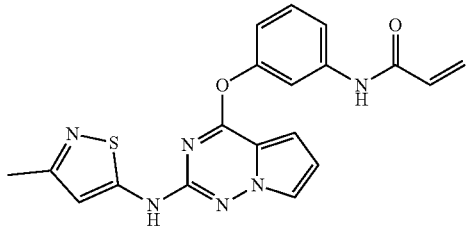 [SMILES: C=CC(=O)Nc1cccc(Oc2nc(Nc3cc(C)ns3)nn3cccc23)c1]

An intermediate N-(3-((2-N-chloropyrrolo[2,1-f][1,2,4]triazin-4-yl)oxy)phenyl)acrylamide was prepared in the same manner as in Example 1, except that 5-amino-phenol was used instead of 5-amino-2-fluorophenol in Example 1.

N-(3-((2-N-chloropyrrolo[2,1-f][1,2,4]triazin-4-yl)oxy)phenyl)acrylamide (50.0 mg, 1.0 eq) was dissolved in t-butanol/N,N-dimethylformamide (3.0 mL/0.6 mL). After adding 3-methylisothiazol-5-amine (16.3 mg, 0.9 eq), Pd$_2$(dba)$_3$ (7.3 mg, 0.05 eq), Xphos (7.6 mg, 0.1 eq) and K$_2$CO$_3$ (48.3 mg, 2.2 eq), N$_2$ gas purge was done for 30 minutes. The reaction solution was stirred at 150° C. for 16 hours and the reaction was terminated. The reaction solution was concentrated under reduced pressure. Extraction was performed by adding ethyl acetate and distilled water. Then, the extracts were dried over anhydrous sodium sulfate, and concentrated under reduced pressure. The resulting residue was purified by column chromatography (ethyl acetate:hexane=1:1) to obtain N-(3-((2-((3-methylisothiazol-5-yl)amino)pyrrolo[2,1-f][1,2,4]triazin-4-yl)oxy)phenyl)acrylamide (3.5 mg, 6.2%).

$^1$H NMR (500 MHz, CD$_3$OD) δ 7.75-7.74 (m, 2H), 7.55-7.53 (m, 1H), 7.44 (t, 1H), 7.06-7.05 (m, 1H), 6.99-6.98 (m, 1H), 6.76-6.75 (m, 1H), 6.50 (s, 1H), 6.45-6.34 (m, 2H), 5.78 (dd, 1H), 2.28 (s, 3H)

Example 6

Preparation of N-(3-((2-((1-ethyl-1H-pyrazol-4-yl)amino)pyrrolo[2,1-f][1,2,4]triazin-4-yl)oxy)phenyl)acrylamide

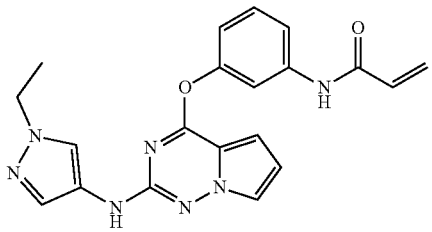 [SMILES: C=CC(=O)Nc1cccc(Oc2nc(Nc3cnn(CC)c3)nn3cccc23)c1]

A title compound (7.3 mg, yield: 19.7%) was obtained in the same manner as in Example 1, except that 1-ethyl-1H-pyrazol-4-amine was used instead of 1-cyclopropyl-1H-pyrazole-4-amine, and 5-amino-phenol was used instead of 5-amino-2-fluorophenol in Example 1.

$^1$H NMR (500 MHz, CD$_3$OD) δ 7.75 (br s, 1H), 7.70 (s, 1H), 7.61 (s, 1H), 7.57-7.55 (m, 1H), 7.43 (t, 1H), 7.37 (s, 1H), 7.04-7.03 (m, 1H), 6.85-6.84 (m, 1H), 6.63-6.62 (m, 1H), 6.45-6.34 (m, 2H), 5.79-5.77 (m, 1H), 4.06-4.04 (m, 2H), 1.38 (t, 3H)

Example 7

Preparation of N-(4-fluoro-3-((2-((3-methylisothiazol-5-yl)amino)pyrrolo[2,1-f][1,2,4]triazin-4-yl)oxy)phenyl)acrylamide

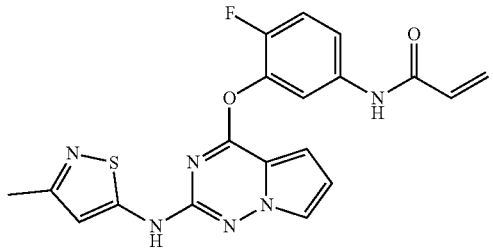 [SMILES: C=CC(=O)Nc1ccc(F)c(Oc2nc(Nc3cc(C)ns3)nn3cccc23)c1]

A title compound (3.6 mg, yield: 6.5%) was obtained in the same manner as in Example 5, except that 5-amino-2-fluorophenol was used instead of 5-amino-phenol in Example 5.

$^1$H NMR (500 MHz, CD$_3$OD) δ 7.87-7.86 (m, 1H), 7.78 (s, 1H), 7.56-7.55 (m, 1H), 7.29 (t, 1H), 7.03-7.02 (m, 1H), 6.79 (s, 1H), 6.51 (s, 1H), 6.44-6.35 (m, 2H), 5.79-5.78 (m, 1H), 2.28 (s, 3H)

Example 8

Preparation of N-(3-((2-((1-ethyl-1H-pyrazol-4-yl)amino)pyrrolo[2,1-f][1,2,4]triazin-4-yl)oxy)-4-fluorophenyl)acrylamide

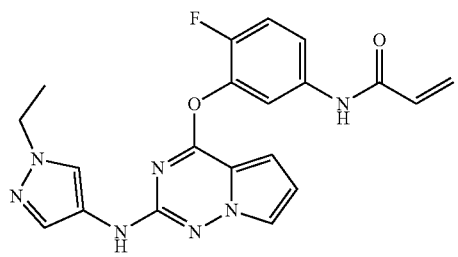 [SMILES: C=CC(=O)Nc1ccc(F)c(Oc2nc(Nc3cnn(CC)c3)nn3cccc23)c1]

A title compound (4.9 mg, yield: 13.3%) was obtained in the same manner as in Example 1, except that 1-ethyl-1H-pyrazol-4-amine was used instead of 1-cyclopropyl-1H-pyrazol-4-amine in Example 1.

$^1$H NMR (500 MHz, CD$_3$OD) δ 7.80-7.78 (m, 2H), 7.65 (s, 1H), 7.57-7.54 (m, 1H), 7.39 (s, 1H), 7.27 (t, 1H), 6.89-6.88 (m, 1H), 6.66-6.64 (m, 1H), 6.40-6.35 (m, 2H), 5.80-5.77 (m, 1H), 4.07 (q, 2H), 1.40 (t, 3H)

Example 9

Preparation of N-(4-fluoro-3-((2-((1-methyl-1H-pyrrol-3-yl)amino)pyrrolo[2,1-f][1,2,4]triazin-4-yl)oxy)phenyl)acrylamide

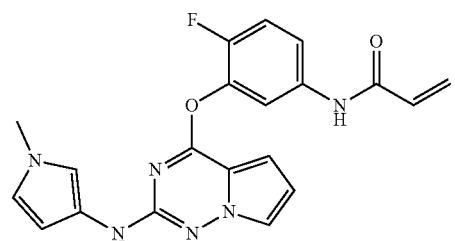

A title compound (9.6 mg, yield: 20.0%) was prepared in the same manner as in Example 1, except that 1-methyl-1H-pyrrole-3-amine was used instead of 1-cyclopropyl-1H-pyrazol-4-amine in Example 1.

$^1$H NMR (500 MHz, CD$_3$OD) δ 7.76-7.74 (m, 1H), 7.59-7.54 (m, 2H), 7.26 (t, 1H), 6.95 (br s, 1H), 6.84 (dd, 1H), 6.61 (dd, 1H), 6.42-6.35 (m, 3H), 5.89-5.88 (m, 1H), 5.78 (dd, 1H), 3.57 (s, 3H)

Example 10

Preparation of N-(4-fluoro-3-((2-((1-isobutyl-1H-pyrazol-4-yl)amino)pyrrolo[2,1-f][1,2,4]triazin-4-yl)oxy)phenyl)acrylamide

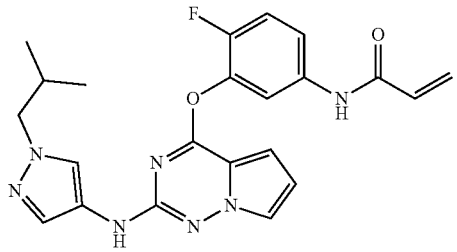 [SMILES: C=CC(=O)Nc1ccc(F)c(Oc2nc(Nc3cnn(CC(C)C)c3)nn3cccc23)c1]

A title compound (2.0 mg, yield: 5.1%) was obtained in the same manner as in Example 1, except that 1-isobutyl-1H-pyrazol-4-amine was used instead of 1-cyclopropyl-1H-pyrazol-4-amine in Example 1.

$^1$H NMR (500 MHz, CD$_3$OD) δ 7.79-7.78 (m, 1H), 7.72-7.71 (m, 1H), 7.65 (s, 1H), 7.59-7.57 (m, 1H), 7.40-7.38 (m, 1H), 7.28 (t, 1H), 6.89 (d, 1H), 6.66-6.65 (m, 1H), 6.46-6.35 (m, 2H), 5.79 (dd, 1H), 3.93 (dd, 1H), 3.81 (d, 2H), 2.03-2.02 (m, 6H)

Example 11

Preparation of N-(3-((2-((1-cyclopropyl-1H-pyrazol-4-yl)amino)pyrrolo[2,1-f][1,2,4]triazin-4-yl)oxy)phenyl)acrylamide

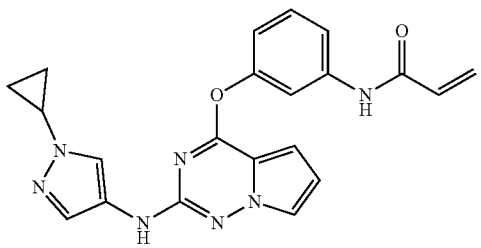 [SMILES: C=CC(=O)Nc1cccc(Oc2nc(Nc3cnn(C4CC4)c3)nn3cccc23)c1]

A title compound (7.8 mg, yield: 15.3%) was obtained in the same manner as in Example 1, except that 5-aminophenol was used instead of 5-amino-2-fluorophenol in Example 1.

$^1$H NMR (500 MHz, CD$_3$OD) δ 7.76 (br s, 1H), 7.70-7.69 (m, 1H), 7.62 (t, 1H), 7.56 (d, 1H), 7.43 (t, 1H), 7.36 (s, 1H), 7.03 (dd, 1H), 6.85 (dd, 1H), 6.63 (dd, 1H), 6.45-6.34 (m, 2H), 5.78 (dd, 1H), 3.50-3.49 (m, 1H), 0.99-0.97 (m, 4H)

Example 12

Preparation of N-(3-((2-((4-(dimethylamino)phenyl)amino)pyrrolo[2,1-f][1,2,4]triazin-4-yl)oxy)-4-fluorophenyl)acrylamide

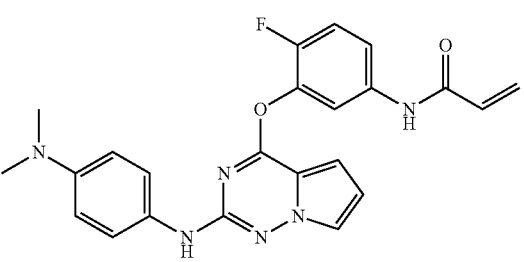

A title compound (5.3 mg, yield: 13.6%) was obtained in the same manner as in Example 1, except that N$^1$,N$^1$-dimethylbenzene-1,4-diamine was used instead of 1-cyclopropyl-1H-pyrazol-4-amine in Example 1.

$^1$H NMR (500 MHz, CD$_3$OD) δ 7.78 (dd, 1H), 7.60-7.59 (m, 1H), 7.57-7.54 (m, 1H), 7.42-7.40 (m, 2H), 7.26 (t, 1H), 6.87-6.86 (m, 1H), 6.77-6.74 (m, 2H), 6.64-6.63 (m, 1H), 6.44-6.35 (m, 2H), 5.78 (dd, 1H), 2.84 (s, 6H)

Example 13

Preparation of N-(4-fluoro-3-((2-((4-phenoxyphenyl)amino)pyrrolo[2,1-f][1,2,4]triazin-4-yl)oxy)phenyl)acrylamide

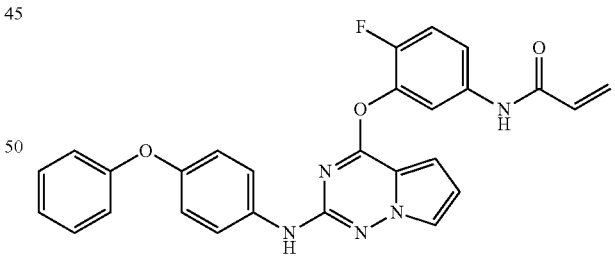

A title compound (9.2 mg, yield: 21.2%) was obtained in the same manner as in Example 1, except that 4-phenoxyaniline was used instead of 1-cyclopropyl-1H-pyrazol-4-amine in Example 1.

$^1$H NMR (500 MHz, CD$_3$OD) δ 7.81-7.79 (m, 1H), 7.64-7.63 (m, 1H), 7.57-7.51 (m, 3H), 7.31-7.24 (m, 3H), 7.03 (t, 1H), 6.91-6.86 (m, 5H), 6.66 (dd, 1H), 6.40-6.34 (m, 2H), 5.78 (dd, 1H)

Example 14

Preparation of N-(3-((2-((benzo[d]thiazol-6-yl)amino)pyrrolo[2,1-f][1,2,4]triazin-4-yl)oxy)-4-fluorophenyl)acrylamide

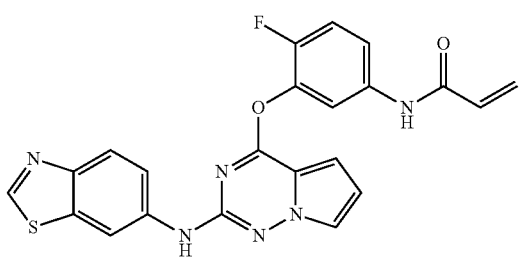 [SMILES: C=CC(=O)Nc1ccc(F)c(Oc2nc(Nc3ccc4ncsc4c3)nn3cccc23)c1]

A title compound (8.6 mg, yield: 21.4%) was prepared in the same manner as in Example 1, except that 4-benzo[d]thiazol-6-amine was used instead of 1-cyclopropyl-1H-pyrazol-4-amine in Example 1.

$^1$H NMR (500 MHz, CD$_3$OD) δ 9.01 (s, 1H), 8.55 (d, 1H), 7.86-7.84 (m, 2H), 7.76-7.75 (m, 1H), 7.59-7.56 (m, 1H), 7.50 (dd, 1H), 7.30 (t, 1H), 6.98 (dd, 1H), 6.73 (dd, 1H), 6.41-6.35 (m, 2H), 5.78 (dd, 1H)

Example 15

Preparation of N-(4-fluoro-3-((2-((pyridin-3-yl)amino)pyrrolo[2,1-f][1,2,4]triazin-4-yl)oxy)phenyl)acrylamide

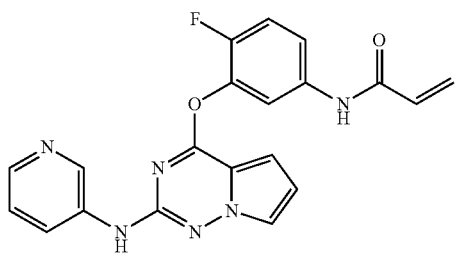 [SMILES: C=CC(=O)Nc1ccc(F)c(Oc2nc(Nc3cccnc3)nn3cccc23)c1]

The same procedures as in Example 1 were carried out except that the step 3 in Example 1 was changed to the following process.

N-(3-((2-chloropyrrolo[2,1-f][1,2,4]triazin-4-yl)oxy)-4-fluorophenyl)acrylamide (20.0 mg, 1.0 eq) and pyridine-3-amine (9.6 mg, 1.7 eq) were dissolved in 2.0 mL of 1,4-dioxane. After adding Pd(OAc)$_2$ (1.2 mg, 0.09 eq), BINAP (6.4 mg, 0.2 eq) and Cs$_2$CO$_3$ (50.9 mg, 2.6 eq), the reaction solution was allowed to react under reflux for 24 hours. Extraction was carried out by adding ethyl acetate and then adding distilled water. Then, the extracts were dried over anhydrous sodium sulfate, and concentrated under reduced pressure. The resulting residue was purified by column chromatography (ethyl acetate:hexane=1:1) to obtain N-(4-fluoro-3-((2-((pyridin-3-yl)amino)pyrrolo[2,1-f][1,2,4]triazin-4-yl)oxy)phenyl)acrylamide (3.0 mg, 12.8%).

$^1$H NMR (500 MHz, CD$_3$OD) δ 8.70 (s, 1H), 8.20-8.19 (m, 1H), 8.07-8.06 (m, 1H), 7.83-7.82 (m, 1H), 7.73 (s, 1H), 7.55-7.53 (m, 1H), 7.33-7.27 (m, 2H), 6.96-6.95 (m, 1H), 6.74-6.73 (m, 1H), 6.44-6.35 (m, 2H), 5.79 (dd, 1H)

Comparative Example 16

Preparation of N-(3-((2-((4-isopropylphenyl)amino)pyrrolo[2,1-f][1,2,4]triazin-4-yl)oxy)phenyl)acrylamide

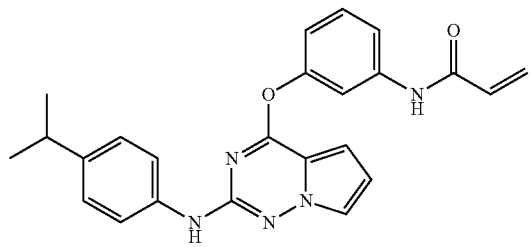 [SMILES: C=CC(=O)Nc1cccc(Oc2nc(Nc3ccc(C(C)C)cc3)nn3cccc23)c1]

A title compound (6.2 mg, yield: 15.7%) was prepared in the same manner as in Example 1, except that 4-isopropylaniline was used instead of 1-cyclopropyl-1H-pyrazol-4-amine, and 3-aminophenol was used instead of 5-amino-2-fluoro phenol in Example 1.

$^1$H NMR (500 MHz, CD$_3$OD) δ 7.71-7.70 (m, 1H), 7.62-7.61 (m, 1H), 7.57-7.55 (m, 1H), 7.47 (d, 2H), 7.46 (t, 1H), 7.08-7.04 (m, 3H), 6.86 (dd, 1H), 6.65-6.63 (m, 1H), 6.46-6.35 (m, 2H), 5.78 (dd, 1H), 2.85-2.79 (m, 1H), 1.20 (d, 6H)

Comparative Example 17

Preparation of N-(3-((2-((4-methoxyphenyl)amino)pyrrolo[2,1-f][1,2,4]triazin-4-yl)oxy)phenyl)acrylamide

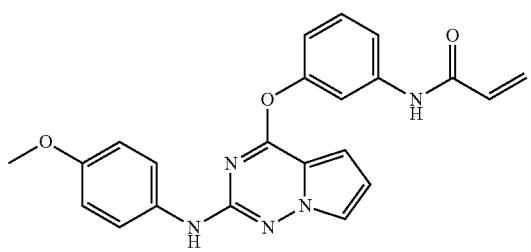 [SMILES: C=CC(=O)Nc1cccc(Oc2nc(Nc3ccc(OC)cc3)nn3cccc23)c1]

A title compound (3.5 mg, yield: 24.8%) was obtained in the same manner as in Example 1, except that 4-methoxyaniline was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.70 (s, 1H), 7.58 (s, 1H), 7.55-7.53 (m, 1H), 7.46 (d, 2H), 7.42 (t, 1H), 7.04 (dd, 1H), 6.84 (dd, 1H), 6.78 (d, 2H), 6.62-6.61 (m, 1H), 6.46-6.35 (m, 2H), 5.78 (dd, 1H), 3.74 (s, 3H)

Comparative Example 18

Preparation of N-(3-((2-((4-(morpholine-4-carbonyl)phenyl)amino)pyrrolo[2,1-f][1,2,4]triazin-4-yl)oxy)phenyl)acrylamide

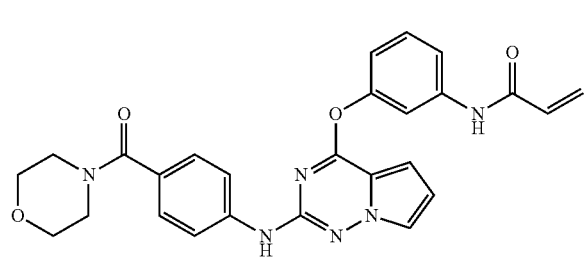 [SMILES: C=CC(=O)Nc1cccc(Oc2nc(Nc3ccc(C(=O)N4CCOCC4)cc3)nn3cccc23)c1]

A title compound (4.0 mg, yield: 8.7%) was prepared in the same manner as in Example 1, except that (4-aminophenyl)(morpholino)methanone was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.72-7.68 (m, 4H), 7.55 (d, 1H), 7.44 (t, 1H), 7.30 (d, 2H), 7.06 (dd, 1H), 6.90 (dd, 1H), 6.70-6.68 (m, 1H), 6.46-6.35 (m, 2H), 5.78 (dd, 1H), 3.67-3.34 (m, 8H)

Comparative Example 19

Preparation of N-(3-((2-((thiophen-3-yl)amino)pyrrolo[2,1-f][1,2,4]triazin-4-yl)oxy)phenyl)acrylamide

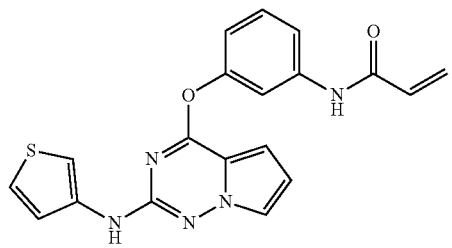 [SMILES: C=CC(=O)Nc1cccc(Oc2nc(Nc3ccsc3)nn3cccc23)c1]

A title compound (7.8 mg, yield: 21.7%) was obtained in the same manner as in Example 1, except that thiophen-3-amine was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.69 (s, 1H), 7.65 (t, 1H), 7.55-7.51 (m, 2H), 7.44-7.40 (m, 1H), 7.20 (dd, 1H), 7.04 (dd, 1H), 6.93 (dd, 1H), 6.86 (dd, 1H), 6.65 (dd, 1H), 6.46-6.34 (m, 2H), 5.78 (dd, 1H)

Comparative Example 20

Preparation of N-(3-((2-((1-methyl-1H-pyrazol-3-yl)amino)pyrrolo[2,1-f][1,2,4]triazin-4-yl)oxy)phenyl)acrylamide

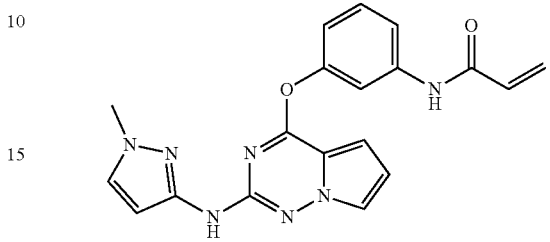

A title compound (8.6 mg, yield: 24.0%) was prepared in the same manner as in Example 1, except that 1-methyl-1H-pyrazole-3-amine was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.70 (s, 1H), 7.62 (s, 1H), 7.55 (d, 1H), 7.42 (t, 1H), 7.35 (d, 1H), 7.04 (dd, 1H), 6.87-6.86 (m, 1H), 6.65-6.64 (m, 1H), 6.45-6.34 (m, 3H), 5.77 (dd, 1H), 3.73 (s, 3H)

Comparative Example 21

Preparation of N-(3-((2-((4-((dimethylamino)methyl)phenyl)amino)pyrrolo[2,1-f][1,2,4]triazin-4-yl)oxy)phenyl)acrylamide

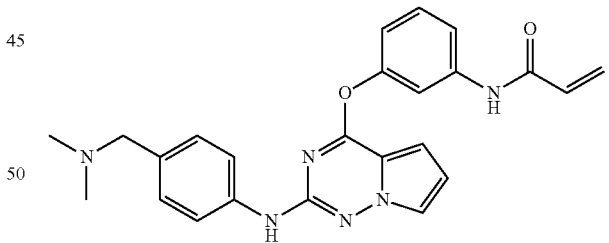

A title compound (4.3 mg, yield: 10.5%) was prepared in the same manner as in Example 1, except that 4-((dimethylamino)methyl)aniline was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.72-7.70 (m, 1H), 7.66-7.63 (m, 3H), 7.56-7.54 (m, 1H), 7.45-7.42 (m, 2H), 7.22 (d, 1H), 7.06 (dd, 1H), 6.89 (dd, 1H), 6.68 (dd, 1H), 6.46-6.35 (m, 2H), 5.79 (dd, 1H), 3.73 (s, 2H), 2.46 (s, 6H)

Comparative Example 22

Preparation of N-(3-((2-((4-morpholinophenyl)amino)pyrrolo[2,1-f][1,2,4]triazin-4-yl)oxy)phenyl)acrylamide

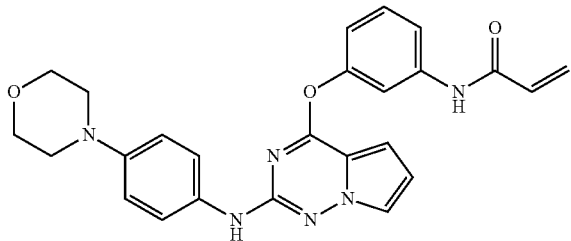 [SMILES: C=CC(=O)Nc1cccc(Oc2nc(Nc3ccc(N4CCOCC4)cc3)nn3cccc23)c1]

A title compound (3.9 mg, yield: 9.0%) was obtained in the same manner as in Example 1, except that 4-morpholinoaniline was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.69 (t, 1H), 7.59-7.55 (m, 2H), 7.48-7.46 (m, 2H), 7.42 (t, 1H), 7.04 (dd, 1H), 6.88-6.84 (m, 3H), 6.63 (dd, 1H), 6.43-6.35 (m, 2H), 5.78 (dd, 1H), 3.81 (t, 4H), 3.04 (t, 4H)

Comparative Example 23

Preparation of N-(3-((2-((4-(dimethylamino)phenyl)amino)pyrrolo[2,1-f][1,2,4]triazin-4-yl)oxy)phenyl)acrylamide

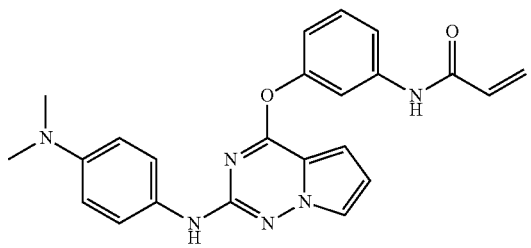 [SMILES: C=CC(=O)Nc1cccc(Oc2nc(Nc3ccc(N(C)C)cc3)nn3cccc23)c1]

A title compound (1.8 mg, yield: 4.6%) was obtained in the same manner as in Example 1, except that N$^1$,N$^1$-dimethylbenzene-1,4-diamine was used instead of 1-cyclopropyl-1H-pyrazol-4-amine, and 5-amino-phenol was used instead of 5-amino-2-fluorophenol in Example 1.

$^1$H NMR (500 MHz, CD$_3$OD) δ 7.69 (t, 1H), 7.57-7.55 (m, 2H), 7.44-7.40 (m, 3H), 7.04 (dd, 1H), 6.84 (dd, 1H), 6.75 (d, 2H), 6.61 (dd, 1H), 6.46-6.35 (m, 2H), 5.78 (dd, 1H), 2.84 (s, 6H)

Example 24

Preparation of N-(3-((2-((5-methyl-4,5,6,7-tetrahydropyrazolo[1,5-a]pyrazin-2-yl)amino)pyrrolo[2,1-f][1,2,4]triazin-4-yl)oxy)phenyl)acrylamide

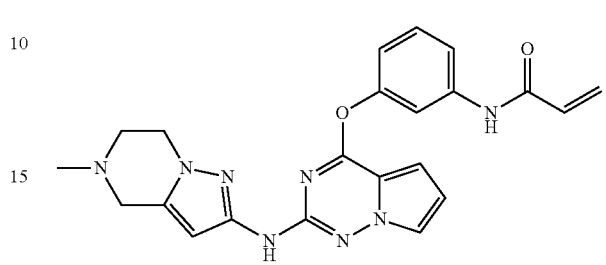

A title compound (6.7 mg, yield: 16.3%) was obtained in the same manner as in Example 1, except that 5-methyl-4,5,6,7-tetrahydropyrazolo[1,5-a]pyrazin-2-amine was used instead of 1-cyclopropyl-1H-pyrazol-4-amine, and 5-aminophenol was used instead of 5-amino-2-fluorophenol in Example 1.

$^1$H NMR (500 MHz, CD$_3$OD) δ 7.68-7.67 (m, 1H), 7.63-7.59 (m, 2H), 7.44 (s, 1H), 7.05-7.03 (m, 1H), 6.88 (dd, 1H), 6.66 (dd, 1H), 6.43-6.38 (m, 2H), 6.20 (s, 1H), 5.79 (dd, 1H), 4.00 (t, 2H), 3.58 (s, 2H), 2.92 (t, 2H), 2.47 (s, 3H)

Example 25

Preparation of N-(4-fluoro-3-((2-((4-(4-methylpiperazin-1-yl)phenyl)amino)pyrrolo[2,1-f][1,2,4]triazin-4-yl)oxy)phenyl)acrylamide

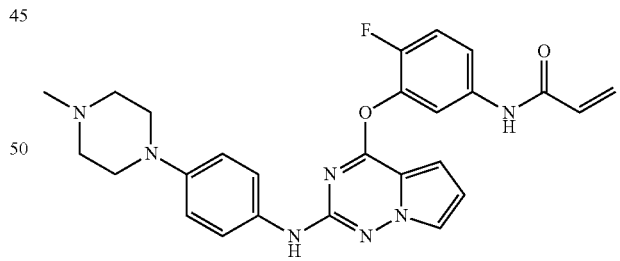

A title compound (14.6 mg, yield: 33.2%) was obtained in the same manner as in Example 1, except that 4-(4-methylpiperazin-1-yl)aniline was used instead of 1-cyclopropyl-1H-pyrazol-4-amine in Example 1.

$^1$H NMR (500 MHz, CD$_3$OD) δ 7.78 (dd, 1H), 7.61 (s, 1H), 7.57-7.54 (m, 1H), 7.46 (d, 2H), 7.26 (t, 1H), 6.89-6.87 (m, 3H), 6.65-6.64 (m, 1H), 6.44-6.34 (m, 2H), 5.78 (dd, 1H), 3.12 (t, 4H), 2.64 (t, 4H), 2.36 (s, 3H)

Example 26

Preparation of N-(3-((2-((1-(2,2-difluoroethyl)-1H-pyrazol-4-yl)amino)pyrrolo[2,1-f][1,2,4]triazin-4-yl)oxy)-4-fluorophenyl)acrylamide

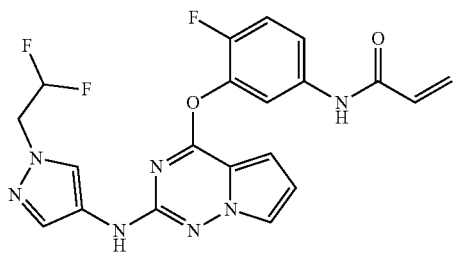 [SMILES: C=CC(=O)Nc1ccc(F)c(Oc2nc(Nc3cnn(CC(F)F)c3)nn3cccc23)c1]

A title compound (16.7 mg, yield: 14.8%) was obtained in the same manner as in Example 1, except that 1-(2,2-difluoroethyl)-1H-pyrazol-4-amine was used instead of 1-cyclopropyl-1H-pyrazol in Example 1.

$^{1}$H NMR (500 MHz, CD$_3$OD) δ 7.90 (s, 1H), 7.79 (dd, 1H), 7.66-7.65 (m, 1H), 7.56-7.53 (m, 1H), 7.46 (s, 1H), 7.26 (t, 1H), 6.89 (dd, 1H), 6.65 (dd, 1H), 6.44-6.34 (m, 2H), 6.10 (td, 1H), 5.79 (dd, 1H), 4.44 (td, 2H)

Example 27

Preparation of N-(4-fluoro-3-((2-((1-methyl-1H-pyrazol-4-yl)amino)pyrrolo[2,1-f][1,2,4]triazin-4-yl)oxy)phenyl)acrylamide

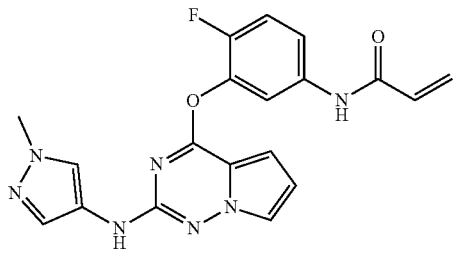 [SMILES: C=CC(=O)Nc1ccc(F)c(Oc2nc(Nc3cnn(C)c3)nn3cccc23)c1]

A title compound (12.6 mg, yield: 35.5%) was obtained in the same manner as in Example 1, except that 1-methyl-1H-pyrazol-4-amine was used instead of 1-cyclopropyl-1H-pyrazol-4-amine in Example 1.

$^{1}$H NMR (500 MHz, CD$_3$OD) δ 7.79-7.77 (m, 2H), 7.65-7.64 (m, 1H), 7.56-7.53 (m, 1H), 7.37 (s, 1H), 7.26 (t, 1H), 6.88 (dd, 1H), 6.64 (dd, 1H), 6.44-6.34 (m, 2H), 5.78 (dd, 1H), 3.79 (s, 3H)

Example 28

Preparation of N-(4-fluoro-3-((2-((4-methoxyphenyl)amino)pyrrolo[2,1-f][1,2,4]triazin-4-yl)oxy)phenyl)acrylamide

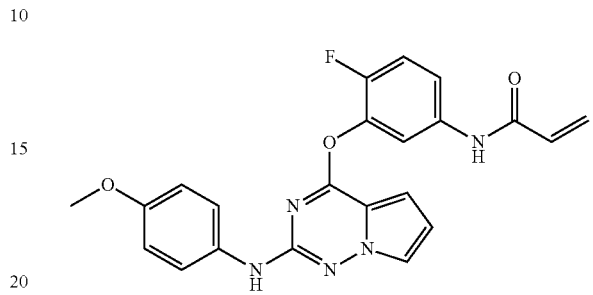

A title compound (9.0 mg, yield: 23.8%) was obtained in the same manner as in Example 1, except that 4-methoxyaniline was instead of 1-cyclopropyl-1H-pyrazol-4-amine.

$^{1}$H NMR (500 MHz, CD$_3$OD) δ 7.78 (dd, 1H), 7.61 (s, 1H), 7.56-7.53 (m, 1H), 7.46 (d, 2H), 7.27 (t, 1H), 6.88 (dd, 1H), 6.79 (d, 2H), 6.66-6.64 (m, 1H), 6.44-6.35 (m, 2H), 5.79 (dd, 1H), 3.74 (s, 3H)

Example 29

Preparation of N-(4-fluoro-3-((2-((4-(morpholine-4-carbonyl)phenyl)amino)pyrrolo[2,1-f][1,2,4]triazin-4-yl)oxy)phenyl)acrylamide

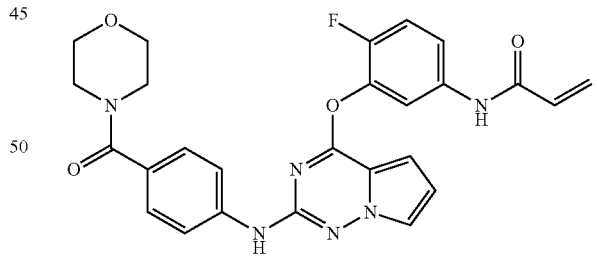

A title compound (14.2 mg, yield: 31.3%) was obtained in the same manner as in Example 1, except that (4-aminophenyl)(morpholino)methanone was used instead of 1-cyclopropyl-1H-pyrazol-4-amine in Example 1.

$^{1}$H NMR (500 MHz, CD$_3$OD) δ 7.81 (dd, 1H), 7.71-7.67 (m, 3H), 7.57-7.52 (m, 1H), 7.39-7.27 (m, 3H), 6.94 (dd, 1H), 6.73-6.71 (m, 1H), 6.44-6.35 (m, 2H), 5.79 (dd, 1H), 3.70-3.62 (m, 8H)

Example 30

Preparation of N-(4-fluoro-3-((2-((thiophen-3-yl)amino)pyrrolo[2,1-f][1,2,4]triazin-4-yl)oxy)phenyl)acrylamide

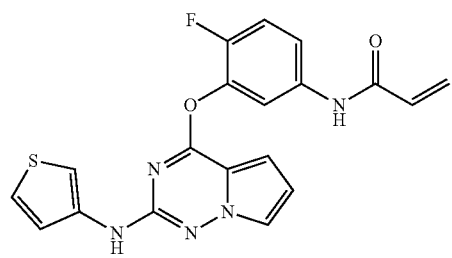 [SMILES: C=CC(=O)Nc1ccc(F)c(Oc2nc(Nc3ccsc3)nn3cccc23)c1]

A title compound (8.2 mg, yield: 22.7%) was obtained in the same manner as in Example 1, except that thiophen-3-amine was used instead of 1-cyclopropyl-1H-pyrazol-4-amine in Example 1.

$^1$H NMR (500 MHz, CD$_3$OD) δ 7.79 (dd, 1H), 7.69-7.56 (m, 1H), 7.56-7.52 (m, 2H), 7.27 (t, 1H), 7.20 (dd, 1H), 6.92 (qd, 2H), 6.68 (dd, 1H), 6.44-6.34 (m, 2H), 5.77 (dd, 1H)

Example 31

Preparation of N-(4-fluoro-3-((2-((4-morpholinophenyl)amino)pyrrolo[2,1-f][1,2,4]triazin-4-yl)oxy)phenyl)acrylamide

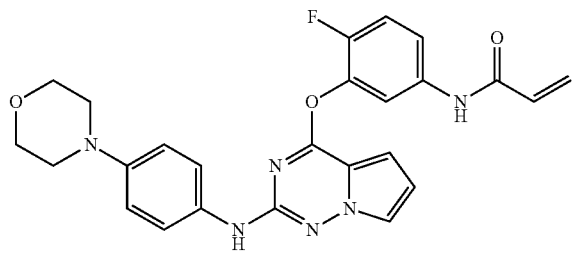 [SMILES: C=CC(=O)Nc1ccc(F)c(Oc2nc(Nc3ccc(N4CCOCC4)cc3)nn3cccc23)c1]

A title compound (5.6 mg, yield: 13.1%) was obtained in the same manner as in Example 1, except that 4-morpholinoaniline was used instead of 1-cyclopropyl-1H-pyrazol-4-amine in Example 1.

$^1$H NMR (500 MHz, CD$_3$OD) δ 7.78 (dd, 1H), 7.62-7.61 (m, 1H), 7.57-7.54 (m, 1H), 7.46 (d, 2H), 7.27 (t, 1H), 6.89-6.86 (m, 3H), 6.65 (dd, 1H), 6.44-6.35 (m, 2H), 5.79 (dd, 1H), 3.81 (t, 4H), 3.04 (t, 4H)

Example 32

Preparation of N-(4-fluoro-3-((2-((1-propyl-1H-pyrazol-4-yl)amino)pyrrolo[2,1-f][1,2,4]triazin-4-yl)oxy)phenyl)acrylamide

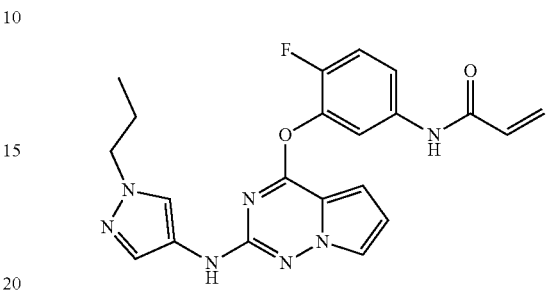

A title compound (6.5 mg, yield: 17.1%) was obtained in the same manner as in Example 1, except that 1-propyl-1H-pyrazol-4-amine was used instead of 1-cyclopropyl-1H-pyrazol-4-amine in Example 1.

$^1$H NMR (500 MHz, CD$_3$OD) δ 7.79 (dd, 1H), 7.78 (s, 1H), 7.65-7.64 (m, 1H), 7.58-7.55 (m, 1H), 7.38 (s, 1H), 7.27 (t, 1H), 6.89 (dd, 1H), 6.65 (dd, 1H), 6.44-6.35 (m, 2H), 5.78 (dd, 1H), 3.98 (t, 2H), 1.80 (q, 2H), 0.88 (t, 3H)

Example 33

Preparation of N-(3-((2-((1-(difluoromethyl)-1H-pyrazol-4-yl)amino)pyrrolo[2,1-f][1,2,4]triazin-4-yl)oxy)-4-fluorophenyl)acrylamide

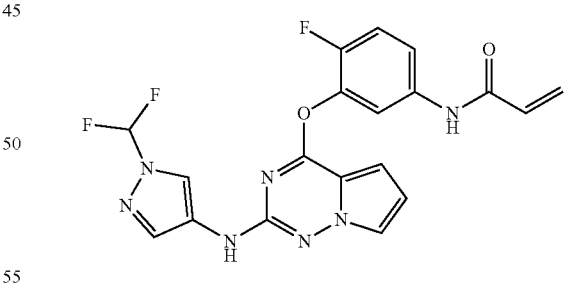

A title compound (6.1 mg, yield: 15.8%) was obtained in the same manner as in Example 1, except that 1-(difluoromethyl)-1H-pyrazol-4-amine was used instead of 1-cyclopropyl-1H-pyrazol-4-amine in Example 1.

$^1$H NMR (500 MHz, CD$_3$OD) δ 8.17 (s, 1H), 7.81 (dd, 1H), 7.71 (s, 1H), 7.60 (s, 1H), 7.55-7.52 (m, 1H), 7.37-7.34 (m, 1H), 7.26 (t, 1H), 6.92 (d, 1H), 6.69 (dd, 1H), 6.44-6.31 (m, 2H), 5.78 (dd, 1H)

Example 34

Preparation of N-(4-fluoro-3-((2-((1-(tetrahydro-2H-pyran-4-yl)-1H-pyrazol-4-yl)amino)pyrrolo[2,1-f][1,2,4]triazin-4-yl)oxy)phenyl)acrylamide

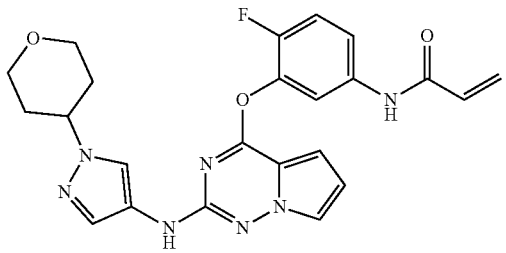 [SMILES: C=CC(=O)Nc1ccc(F)c(Oc2nc(Nc3cnn(C4CCOCC4)c3)nn3cccc23)c1]

A title compound (3.5 mg, yield: 8.4%) was obtained in the same manner as in Example 1, except that 1-(tetrahydro-2H-pyran-4-yl)-1H-pyrazol-4-amine was used instead of 1-cyclopropyl-1H-pyrazol-4-amine in Example 1.

$^1$H NMR (500 MHz, CD$_3$OD) δ 7.81-7.79 (m, 2H), 7.65-7.64 (m, 1H), 7.58-7.56 (m, 1H), 7.40 (s, 1H), 7.27 (t, 1H), 6.88 (dd, 1H), 6.66-6.64 (m, 1H), 6.44-6.34 (m, 2H), 5.78 (dd, 1H), 4.26-4.22 (m, 1H), 4.04-4.02 (m, 2H), 3.56-3.50 (m, 2H), 1.99-1.94 (m, 4H)

Example 35

Preparation of N-(4-fluoro-3-((2-((1-(2-morpholinoethyl)-1H-pyrazol-4-yl)amino)pyrrolo[2,1-f][1,2,4]triazin-4-yl)oxy)phenyl)acrylamide

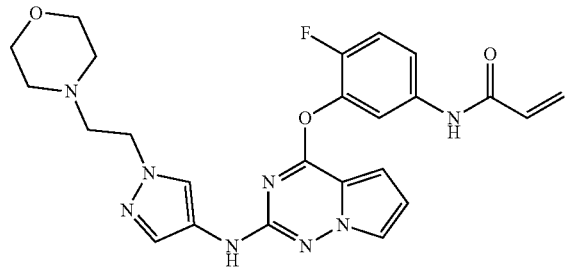 [SMILES: C=CC(=O)Nc1ccc(F)c(Oc2nc(Nc3cnn(CCN4CCOCC4)c3)nn3cccc23)c1]

A title compound (5.4 mg, yield: 12.2%) was obtained in the same manner as in Example 1, except that 1-(2-morpholinoethyl)-1H-pyrazol-4-amine was used instead of 1-cyclopropyl-1H-pyrazol-4-amine in Example 1.

$^1$H NMR (500 MHz, CD$_3$OD) δ 7.89 (s, 1H), 7.78 (dd, 1H), 7.65 (s, 1H), 7.58-7.55 (m, 1H), 7.39 (s, 1H), 7.27 (t, 1H), 6.89 (dd, 1H), 6.65 (dd, 1H), 6.44-6.34 (m, 2H), 5.79 (dd, 1H), 4.19 (t, 2H), 3.67 (t, 4H), 2.75 (t, 2H), 2.46 (t, 4H)

Example 36

Preparation of N-(4-fluoro-3-((2-((1-isopropyl-1H-pyrazol-4-yl)amino)pyrrolo[2,1-f][1,2,4]triazin-4-yl)oxy)phenyl)acrylamide

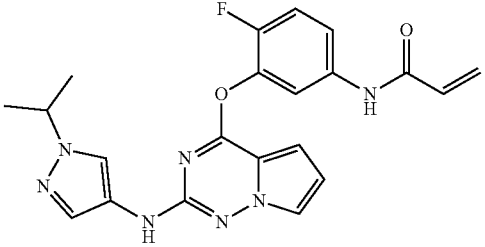 [SMILES: C=CC(=O)Nc1ccc(F)c(Oc2nc(Nc3cnn(C(C)C)c3)nn3cccc23)c1]

A title compound (16.6 mg, yield: 43.7%) was obtained in the same manner as in Example 1, except that 1-isopropyl-1H-pyrazol-4-amine was used instead of 1-cyclopropyl-1H-pyrazol-4-amine in Example 1.

$^1$H NMR (500 MHz, CD$_3$OD) δ 7.80-7.78 (m, 2H), 7.65-7.64 (m, 1H), 7.57-7.55 (m, 1H), 7.41 (s, 1H), 7.26 (t, 1H), 6.88-6.87 (m, 1H), 6.65-6.64 (m, 1H), 6.44-6.35 (m, 2H), 5.78 (dd, 1H), 4.41-4.38 (m, 1H), 1.43 (d, 6H)

Example 37

Preparation of N-(4-fluoro-3-((2-((1-(piperidin-4-yl)-1H-pyrazol-4-yl)amino)pyrrolo[2,1-f][1,2,4]triazin-4-yl)oxy)phenyl)acrylamide

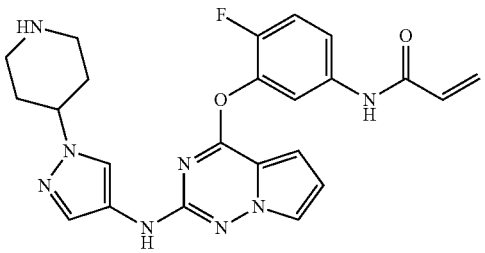 [SMILES: C=CC(=O)Nc1ccc(F)c(Oc2nc(Nc3cnn(C4CCNCC4)c3)nn3cccc23)c1]

A title compound (1.0 mg, yield: 2.4%) was obtained in the same manner as in Example 1, except that tert-butyl 4-(4-amino-1H-pyrazol-1-yl) piperidine-1-carboxylate was used instead of 1-cyclopropyl-1H-pyrazol-4-amine in Example 1.

$^1$H NMR (500 MHz, CD$_3$OD) δ 7.81-7.80 (m, 1H), 7.75-7.74 (m, 1H), 7.64-7.54 (m, 2H), 7.42 (s, 1H), 7.28 (t, 1H), 6.90-6.89 (m, 1H), 6.67-6.66 (m, 1H), 6.44-6.35 (m, 2H), 5.79 (dd, 1H), 4.17-4.16 (m, 1H), 3.20-3.16 (m, 4H), 2.78-2.73 (m, 4H)

Example 38

Preparation of N-(4-fluoro-3-((2-((1-(2,2,2-trifluoroethyl)-1H-pyrazol-4-yl)amino)pyrrolo[2,1-f][1,2,4]triazin-4-yl)oxy)phenyl)acrylamide

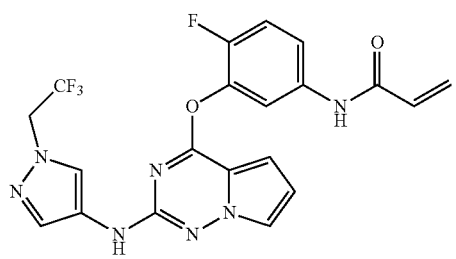 [SMILES: C=CC(=O)Nc1ccc(F)c(Oc2nc(Nc3cnn(CC(F)(F)F)c3)nn3cccc23)c1]

A title compound (7.5 mg, yield: 18.0%) was obtained in the same manner as in Example 1, except that 1-(2,2,2-trifluoroethyl)-1H-pyrazol-4-amine was used instead of 1-cyclopropyl-1H-pyrazol-4-amine in Example 1.

$^1$H NMR (500 MHz, CD$_3$OD) δ 7.97 (br s, 1H), 7.78 (dd, 1H), 7.68-7.67 (m, 1H), 7.57-7.54 (m, 1H), 7.49 (s, 1H), 7.27 (t, 1H), 6.91-6.90 (m, 1H), 6.68-6.66 (m, 1H), 6.44-6.34 (m, 2H), 5.79 (dd, 1H), 4.82-4.79 (m, 2H)

Example 39

Preparation of N-(3-((2-((4-(3,5-dimethyl-1H-pyrazol-1-yl)phenyl)amino)pyrrolo[2,1-f][1,2,4]triazin-4-yl)oxy)-4-fluorophenyl)acrylamide

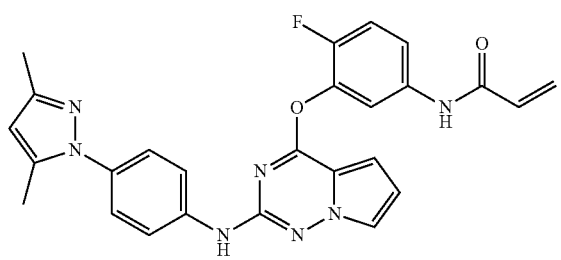 [SMILES: C=CC(=O)Nc1ccc(F)c(Oc2nc(Nc3ccc(-n4nc(C)cc4C)cc3)nn3cccc23)c1]

A title compound (6.0 mg, yield: 13.7%) was obtained in the same manner as in Example 1, except that 4-(3,5-dimethyl-1H-pyrazol-1-yl)aniline was used instead of 1-cyclopropyl-1H-pyrazol-4-amine in Example 1.

$^1$H NMR (500 MHz, CD$_3$OD) δ 7.83-7.81 (m, 1H), 7.73-7.70 (m, 3H), 7.56-7.53 (m, 1H), 7.30-7.26 (m, 1H), 7.23-7.22 (m, 2H), 6.94-6.93 (m, 1H), 6.72-6.70 (m, 1H), 6.45-6.34 (m, 2H), 6.01 (s, 1H), 5.79-5.77 (m, 1H), 2.22-2.21 (m, 6H)

Example 40

Preparation of N-(4-fluoro-3-((2-((1-(2-methoxyethyl)-1H-pyrazol-4-yl)amino)pyrrolo[2,1-f][1,2,4]triazin-4-yl)oxy)phenyl)acrylamide

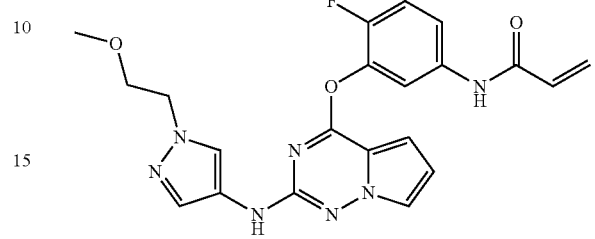

A title compound (1.8 mg, yield: 4.6%) was obtained in the same manner as in Example 1, except that 1-(2-methoxyethyl)-1H-pyrazol-4-amine was used instead of 1-cyclopropyl-1H-pyrazol-4-amine in Example 1.

$^1$H NMR (500 MHz, CD$_3$OD) δ 7.82-7.77 (m, 2H), 7.66-7.65 (m, 1H), 7.57-7.55 (m, 1H), 7.41 (s, 1H), 7.27 (t, 1H), 6.89-6.88 (m, 1H), 6.66-6.65 (m, 1H), 6.44-6.34 (m, 2H), 5.79 (dd, 1H), 4.19 (t, 2H), 3.69 (t, 2H), 2.01 (s, 3H)

Example 41

Preparation of 2-chloro-N-(3-((2-((1-(2,2-difluoroethyl)-1H-pyrazol-4-yl)amino)pyrrolo[2,1-f][1,2,4]triazin-4-yl)oxy)-4-fluorophenyl)acetamide

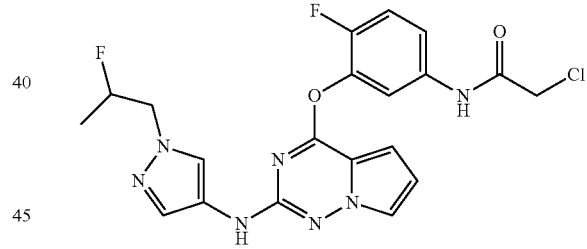

Step 1) Preparation of 2-chloro-4-(2-fluoro-5-nitrophenoxy)pyrrolo[2,1-f][1,2,4]triazine After 2,4-dichloropyrrolo[2,1-f][1,2,4]triazine (500.0 mg, 1.0 eq) and 2-fluoro-5-nitrophenol (438.7 mg, 1.05 eq) were dissolved in N,N-dimethylformamide (10.0 mL), K$_2$CO$_3$ (385.9 mg, 1.05 eq) was added thereto. The reaction solution was stirred at 50° C. for 2 hours, and then cooled to room temperature. Extraction was performed by adding dichloromethane and then adding distilled water. Then, the extracts were dried over anhydrous sodium sulfate, and concentrated under reduced pressure. The resulting residue was purified by column chromatography (ethyl acetate:hexane=1:1) to obtain 2-chloro-4-(2-fluoro-5-nitrophenoxy)pyrrolo[2,1-f][1,2,4]triazine (800.7 mg, 97.6%).

$^1$H NMR (500 MHz, CD$_3$OD) δ 8.44-8.42 (m, 1H), 8.36-8.33 (m, 1H), 7.96-7.95 (m, 1H), 7.61 (t, 1H), 7.20-7.19 (m, 1H), 6.70-6.99 (m, 1H)

Step 2) Preparation of N-(1-(2,2-difluoroethyl)-1H-pyrazol-4-yl)-4-(2-fluoro-5-nitrophenoxy)pyrrolo[1,2-b]triazin-2-amine 2-Chloro-4-(2-fluoro-5-nitrophenoxy)pyrrolo[2,1-f][1,2,4]triazine (200.0 mg, 1.0 eq) and 1-(2,2-difluoroethyl)-1H-pyazol-4-amine (95.3 mg, 1.0 eq) were dissolved in 9.0 mL of 1,4-dioxane. After adding Pd(OAc)₂ (7.3 mg, 0.05 eq), Xanthphos (37.5 mg, 0.1 eq) and Cs₂CO₃ (422.3 mg, 2.0 eq), N₂ gas purge was done for 30 minutes. The reaction solution was reacted using a microwave (150° C., 30 minutes, normal). The reaction solution was filtered, and the filtrate was concentrated under reduced pressure. The obtained concentrated residue was purified by column chromatography (ethyl acetate:hexane=1:1) to obtain N-(1-(2,2-difluoroethyl)-1H-pyrazol-4-yl)-4-(2-fluoro-5-nitrophenoxy)pyrrolo[1,2-b]triazin-2-amine (210.0 mg, 77.5%).

¹H NMR (500 MHz, CD₃OD) δ 8.40-8.39 (m, 1H), 8.32-8.30 (m, 1H), 8.03-7.99 (m, 1H), 7.71 (s, 1H), 7.59 (t, 1H), 7.48 (s, 1H), 6.94-6.93 (m, 1H), 6.69-6.68 (m, 1H), 6.24-6.01 (m, 1H), 4.47 (td, 2H)

Step 3) Preparation of 4-(5-amino-2-fluorophenoxy)-N-(1-(2,2-difluoroethyl)-1H-pyrazol-4-yl)pyrrolo[2,1-f][1,2,4]triazin-2-amine N-(1-(2,2-difluoroethyl)-1H-pyrazol-4-yl)-4-(2-fluoro-5-nitrophenoxy)pyrrolo[1,2-b]triazin-2-amine (210.0 mg, 1.0 eq) was dissolved in 1,4-dioxane/distilled water (3.0 mL/3.0 mL), and then NH₄Cl (214.7 mg, 8.0 eq) was added thereto. The reaction solution was cooled to 0° C. and Zn powder (262.6 mg, 8.0 eq) was added thereto. After stirring at room temperature for 1 hour, the reaction solution was filtered. Extraction was performed by adding dichloromethane to the filtrate and then adding distilled water. Then, the extracts were dried over anhydrous sodium sulfate, and concentrated under reduced pressure. The resulting residue was purified by column chromatography (ethyl acetate:hexane=1:1) to obtain 4-(5-amino-2-fluorophenoxy)-N-(1-(2,2-difluoroethyl)-1H-pyrazol-4-yl)pyrrolo[2,1-f][1,2,4]triazin-2-amine (145.4 mg, 74.6%).

¹H NMR (500 MHz, CD₃OD) δ 7.90 (br s, 1H), 7.46 (s, 1H), 7.13 (t, 1H), 6.95 (m, 1H), 6.88-6.85 (m, 2H), 6.72-6.63 (m, 1H), 6.23-5.99 (m, 1H), 4.45 (td, 2H)

Step 4) Preparation of 2-chloro-N-(3-((2-((1-(2,2-difluoroethyl)-1H-pyrazol-4-yl)amino)pyrrolo[2,1-f][1,2,4]triazin-4-yl)oxy)-4-fluorophenyl)acetamide 4-(5-amino-2-fluorophenoxy)-N-(1-(2,2-difluoroethyl)-1H-pyrazol-4-yl)pyrrolo[2,1-f][1,2,4]triazin-2-amine (20.0 mg, 1.0 eq) and 2-chloroacetic acid (6.7 mg, 1.2 eq) were dissolved in 5.0 mL of THF. O-(7-azabenzotriazol-1-yl)-N,N,N',N'-tetramethylruronium hexafluorophosphate (O-HATU, 27.0 mg, 1.2 eq) and N,N-diisopropylethylamine (15.3 mg, 2.0 eq) were added thereto. The reaction solution was stirred at room temperature for 24 hours and then the reaction was terminated. Extraction was performed by adding ethyl acetate and then adding distilled water. Then, the extracts were dried over anhydrous sodium sulfate, and concentrated under reduced pressure. The resulting residue was purified by column chromatography (ethyl acetate:hexane=1:1) to obtain 2-chloro-N-(3-((2-((1-(2,2-difluoroethyl)-1H-pyrazol-4-yl)amino)pyrrolo[2,1-f][1,2,4]triazin-4-yl)oxy)-4-fluorophenyl)acetamide (9.3 mg, 33.8%).

¹H NMR (500 MHz, CD₃OD) δ 7.90 (br s, 1H), 7.72-7.70 (m, 1H), 7.66-7.65 (m, 1H), 7.53-7.50 (m, 1H), 7.46 (s, 1H), 7.27 (t, 1H), 6.89-6.88 (m, 1H), 6.66-6.65 (m, 1H), 6.11 (tt, 1H), 4.45 (td, 2H), 4.18 (s, 2H)

Example 42

Preparation of 2-chloro-N-(4-fluoro-3-((2-((1-(tetrahydro-2H-pyran-4-yl)-1H-pyrazol-4-yl)amino)pyrrolo[2,1-f][1,2,4]triazin-4-yl)oxy)phenyl)acetamide

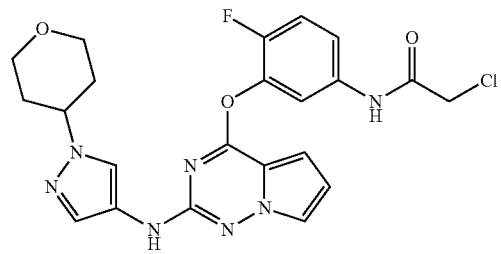 [SMILES: O=C(CCl)Nc1ccc(F)c(Oc2nc(Nc3cnn(C4CCOCC4)c3)nn3cccc23)c1]

A title compound (9.0 mg, yield: 37.9%) was obtained in the same manner as in Example 41, except that 1-(tetrahydro-2H-pyran-4-yl)-1H-pyrazol-4-amine was used instead of 1-(2,2-difluoroethyl)-1H-pyrazol-4-amine in Example 41.

¹H NMR (500 MHz, CD₃OD) δ 7.79-7.71 (m, 2H), 7.66 (s, 1H), 7.55-7.53 (m, 1H), 7.40 (s, 1H), 7.29 (t, 1H), 6.89-6.88 (m, 1H), 6.66-6.65 (m, 1H), 4.30-4.24 (m, 1H), 4.18 (s, 2H), 4.06-4.04 (m, 2H), 3.58-3.53 (m, 2H), 2.03-1.96 (m, 4H)

Example 43

Preparation of 2-chloro-N-(3-((2-((1-ethyl-1H-pyrazol-4-yl)amino)pyrrolo[2,1-f][1,2,4]triazin-4-yl)oxy)-4-fluorophenyl)acetamide

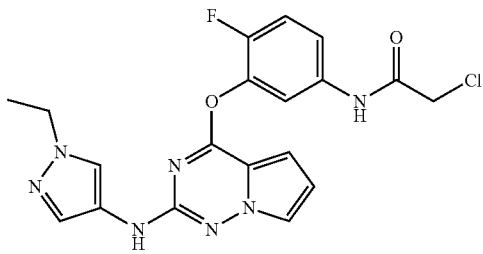 [SMILES: CCn1cc(Nc2nc(Oc3cc(NC(=O)CCl)ccc3F)c3cccn3n2)cn1]

A title compound (9.1 mg, yield: 43.3%) was obtained in the same manner as in Example 41, except that 1-ethyl-1H-pyrazol-4-amine was used instead of 1-(2,2-difluoroethyl)-1H-pyrazol-4-amine in Example 41.

¹H NMR (500 MHz, CD₃OD) δ 7.77 (br s, 1H), 7.72-7.70 (m, 1H), 7.66-7.65 (m, 1H), 7.54-7.51 (m, 1H), 7.39 (s, 1H), 7.28 (t, 1H), 6.89-6.87 (m, 1H), 6.65-6.64 (m, 1H), 4.18 (s, 2H), 4.08 (q, 2H), 1.40 (t, 3H)

Example 44

Preparation of (E)-4-chloro-N-(3-((2-((1-ethyl-1H-pyrazol-4-yl)amino)pyrrolo[2,1-f][1,2,4]triazin-4-yl)oxy)-4-fluorophenyl)but-2-enamide

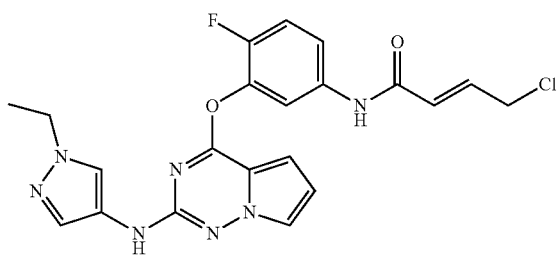 [SMILES: CCn1cc(Nc2nc(Oc3cc(NC(=O)/C=C/CCl)ccc3F)c3cccn3n2)cn1]

A title compound (8.1 mg, yield: 36.4%) was obtained in the same manner as in Example 41, except that 1-ethyl-1H-pyrazol-4-amine was used instead of 1-(2,2-difluoroethyl)-1H-pyrazol-4-amine, and (E)-4-chlorobut-2-enoic acid was used instead of 2-chloroacetic acid.

¹H NMR (500 MHz, CD₃OD) δ 7.77 (s, 1H), 7.70-7.68 (m, 1H), 7.65-7.64 (m, 1H), 7.49-7.47 (m, 1H), 7.38 (s, 1H), 7.25 (t, 1H), 6.88-6.87 (m, 1H), 6.65-6.64 (m, 1H), 6.35-3.33 (m, 1H), 6.13-6.10 (m, 1H), 4.07 (q, 2H), 3.39-3.37 (m, 2H), 1.40 (t, 3H)

Example 45

Preparation of N-(4-fluoro-3-(2-(isoxazol-4-ylamino)pyrrolo[2,1-f][1,2,4]triazin-4-yloxy)phenyl)acrylamide

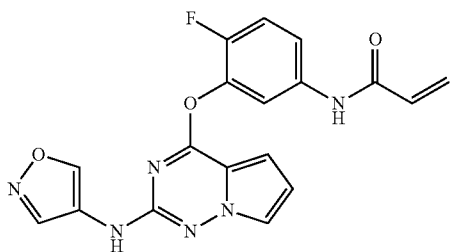 [SMILES: C=CC(=O)Nc1ccc(F)c(Oc2nc(Nc3cnoc3)nn3cccc23)c1]

An intermediate N-(4-(5-amino-2-fluorophenoxy)pyrrolo[2,1-f][1,2,4]triazin-2-yl)isoxazol-4-amine was prepared in the same manner as in Example 41, except that isoxazol-4-amine was used instead of I-(2,2-difluoroethyl)-IH-pyrazol-4-amine in Example 41.

N-(4-(5-amino-2-fluorophenoxy)pyrrolo[2,1-f][1,2,4]triazin-2-yl)isoxazol-4-amine (7.5 mg, 1.0 eq) was dissolved in 1.0 mL of dichloromethane and then cooled to 0° C. N,N-diisopropylethylamine (5.9 mg, 2.0 eq) was added and then acryloyl chloride (2.2 mg, 1.05 eq) was added dropwise. The reaction solution was stirred at 0° C. for 30 minutes to terminate the reaction. Extraction was performed by adding ethyl acetate and then adding distilled water. Then, the extracts were dried over anhydrous sodium sulfate, and concentrated under reduced pressure. The resulting residue was purified by column chromatography (dichloromethane:methanol=10:1) to obtain N-(4-fluoro-3-(2-(isoxazol-4-ylamino)pyrrolo[2,1-f][1,2,4]triazin-4-yloxy)phenyl)acrylamide (1.7 mg, 19.5%).

¹H NMR (500 MHz, CD₃OD) δ 8.95 (br s, 1H), 8.32 (s, 1H), 7.81 (dd, 1H), 7.74-7.73 (m, 1H), 7.54-7.53 (m, 1H), 7.27 (t, 1H), 6.94-6.93 (m, 1H), 6.71-6.70 (m, 1H), 6.44-6.35 (m, 2H), 5.79 (dd, 1H)

Example 46

Preparation of N-(4-chloro-3-((2-((1-ethyl-1H-pyrazol-4-yl)amino)pyrrolo[2,1-f][1,2,4]triazin-4-yl)oxy)phenyl)acrylamide

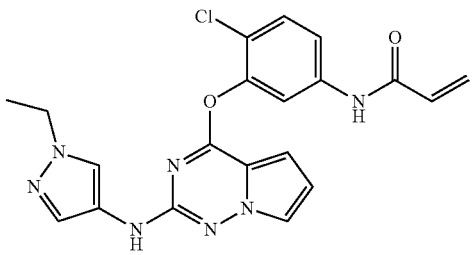 [SMILES: C=CC(=O)Nc1ccc(Cl)c(Oc2nc(Nc3cnn(CC)c3)nn3cccc23)c1]

A title compound (1.4 mg, yield: 3.8%) was obtained in the same manner as in Example 1, except that ethyl-1H-pyrazol-4-amine was used instead of 1-cyclopropyl-1H-pyrazol-4-amine, and 5-amino-2-chlorophenol was used instead of 5-amino-2-fluorophenol in Example 1.

¹H NMR (500 MHz, CD₃OD) δ 7.83-7.81 (m, 1H), 7.72-7.70 (m, 1H), 7.66-7.65 (m, 1H), 7.61-7.56 (m, 1H), 7.51-7.50 (m, 1H), 7.37-7.36 (m, 1H), 6.90-6.89 (m, 1H), 6.66-6.65 (m, 1H), 6.44-6.36 (m, 2H), 5.80 (dd, 1H), 4.09-4.05 (m, 2H), 1.44-1.41 (m, 3H)

Example 47

Preparation of N-(5-((2-((1-ethyl-1H-pyrazol-4-yl)amino)pyrrolo[2,1-f][1,2,4]triazin-4-yl)oxy)-2-methylphenyl)acrylamide

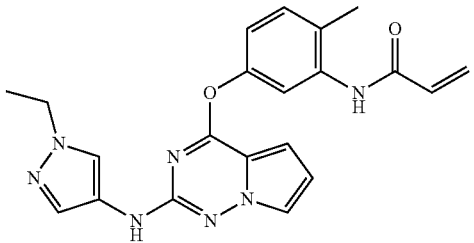 [SMILES: C=CC(=O)Nc1cc(Oc2nc(Nc3cnn(CC)c3)nn3cccc23)ccc1C]

A title compound (3.4 mg, yield: 9.2%) was obtained in the same manner as in Example 1, except that 1-ethyl-1H-pyrazol-4-amine was used instead of 1-cyclopropyl-1H-pyrazol-4-amine, and 3-amino-4-methylphenol was used instead of 5-amino-2-fluorophenol in Example 1.

¹H NMR (500 MHz, CD₃OD) δ 7.77 (br s, 1H), 7.61-7.60 (m, 1H), 7.49-7.48 (m, 1H), 7.38 (s, 1H), 7.35-7.34 (m, 1H), 7.08-7.06 (m, 1H), 6.84-6.83 (m, 1H), 6.62-6.61 (m, 1H), 6.53-6.51 (m, 1H), 6.39-6.35 (m, 1H), 5.79 (dd, 1H), 4.07 (q, 2H), 2.31 (s, 3H), 1.39 (t, 3H)

Example 48

Preparation of N-(5-((2-((1-(2,2-difluoroethyl)-1H-pyrazol-4-yl)amino)pyrrolo[2,1-f][1,2,4]triazin-4-yl)oxy)-2-methylphenyl)acrylamide

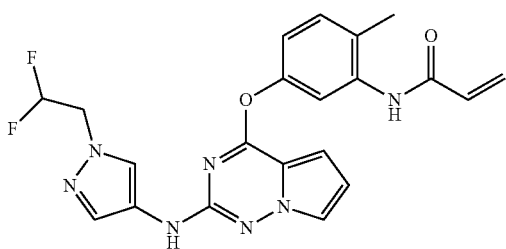 [SMILES: C=CC(=O)Nc1cc(Oc2nc(Nc3cnn(CC(F)F)c3)nn3cccc23)ccc1C]

A title compound (6.3 mg, yield: 15.7%) was obtained in the same manner as in Example 1, except that 1-(2,2-difluoroethyl)-1H-pyrazol-4-amine was used instead of 1-cyclopropyl-1H-pyrazol-4-amine, and 3-amino-4-methylphenol was used instead of 5-amino-2-fluorophenol in Example 1.

$^1$H NMR (500 MHz, CD$_3$OD) δ 7.87 (br s, 1H), 7.62-7.61 (m, 1H), 7.48-7.44 (m, 2H), 7.35-7.33 (m, 1H), 7.08-7.06 (m, 1H), 6.85-6.84 (m, 1H), 6.63-6.62 (m, 1H), 6.56-6.51 (m, 1H), 6.39-6.35 (m, 1H), 6.20-5.98 (m, 1H), 5.80-5.78 (m, 1H), 4.43 (td, 2H), 2.31 (s, 3H)

Example 49

Preparation of N-(3-((2-((1-(2,2-difluoroethyl)-1H-pyrazol-4-yl)amino)pyrrolo[2,1-f][1,2,4]triazin-4-yl)oxy)-4-fluorophenyl)pent-2-ynamide

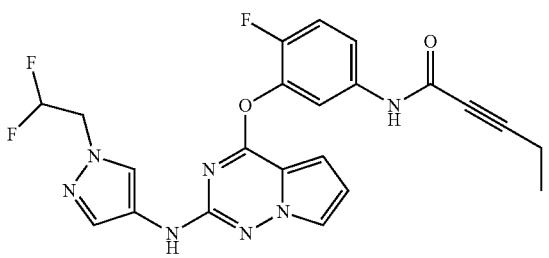 [SMILES: CCC#CC(=O)Nc1ccc(F)c(Oc2nc(Nc3cnn(CC(F)F)c3)nn3cccc23)c1]

A title compound (2.1 mg, yield: 7.6%) was obtained in the same manner as in Example 41, except that pent-2-enoic acid was used instead of 2-chloroacetic acid in Example 41.

$^1$H NMR (500 MHz, CD$_3$OD) δ 7.91 (br s, 1H), 7.67-7.65 (m, 2H), 7.53-7.50 (m, 1H), 7.47 (s, 1H), 7.25 (t, 1H), 6.92-6.88 (m, 1H), 6.68-6.65 (m, 1H), 6.23-5.99 (m, 1H), 4.45 (td, 2H), 2.41 (q, 2H), 1.23 (t, 3H)

Experimental Example: Measurement of JAK 3 and BTK Enzyme Inhibitory Activity JAK3 and BTK kinase inhibitory activities were measured for the compounds prepared in the above Examples through in vitro analysis on the ADP Glow (Glo) platform.

Specifically, the inhibitory activities of JAK3 and BTK kinase were measured using a JAK3 kinase assay kit (Promega, V9441) and a BTK kinase assay kit (Promega, V9071) which were purchased from Promega. Recombinant purified human JAK3 and BTK were diluted with 1× kinase reaction buffer (JAK3: 40 mM Tris-Cl, pH 7.5, 20 mM MgCl$_2$, 0.1 mg/mL BSA and 50 uM DTT/BTK: 40 mM Tris-Cl, pH 7.5, 20 mM MgCl$_2$, 0.1 mg/mL BSA, 2 mM MnCl$_2$ and 50 uM DTT) and added to a 96 well plate (JAK3: final concentration of 4 ng per reaction/BTK: final concentration of 8 ng per reaction). The compounds were treated so as to be finally a 1% DMSO aqueous solution, and a substrate cocktail containing ATP (JAK3: final concentration of 5 uM/BTK: final concentration of 10 uM) and 0.2 ug/uL of Poly(Glu4, Tyr1)peptide (JAK3 and BTK final concentration) in the total 25 uL reactants was added to a 96-well plate to initiate enzymatic reaction. After incubation (30° C.) for 1 hour, equivalent volume (25 uL per reaction) of ADP Glo was added and incubated (30° C.) for 40 minutes at room temperature. Then, a kinase detection reagent (50 uL per reaction) was added and incubated (30° C.) for 30 minutes at room temperature. The kinase activity was measured by chemiluminescence according to the instructions of ADP Glo kinase assay kit, and the inhibitory activity of the compounds according to the present invention was calculated. For the analysis of the results of each compound, Microsoft Excel was used, and IC$_{50}$ values were calculated by SigmaPlot software. The results are shown in Table 1 below.

TABLE 1

| Example No. | JAK3 IC$_{50}$ (nM) | BTK IC$_{50}$ (nM) |
|---|---|---|
| 1 | 1.1 | 13.6 |
| 2* | 2.8 | 22.7 |
| 3 | 0.6 | 12.7 |
| 4 | 0.7 | 13.4 |
| 5 | 0.6 | 8.7 |
| 6 | 0.5 | 10.0 |
| 7 | 0.5 | 10.7 |
| 8 | 0.6 | 7.7 |
| 9 | 16.8 | 243.4 |
| 10 | 9.6 | 112.9 |
| 11 | 10.3 | 107.2 |
| 12 | 0.7 | 7.5 |
| 13 | 41.7 | 622.4 |
| 14 | 9.8 | 43.3 |
| 15 | 15.5 | 103.5 |
| 16* | 20.0 | 123.1 |
| 17* | 5.9 | 68.6 |
| 18* | 2.2 | 37.8 |
| 19* | 5.3 | 62.9 |
| 20* | 57.7 | 647.3 |
| 21* | 11.7 | 103.8 |
| 22* | 5.3 | 35.4 |
| 23* | 10.4 | 60.2 |
| 24 | 18.8 | 166.4 |
| 25 | 1.4 | 7.9 |
| 26 | 0.9 | 6.2 |
| 27 | 0.7 | 5.0 |
| 28 | 9.2 | 52.0 |
| 29 | 2.0 | 23.1 |
| 30 | 7.6 | 66.6 |
| 31 | 4.5 | 27.4 |
| 32 | 1.4 | 9.1 |
| 33 | 2.8 | 15.3 |
| 34 | 0.5 | 2.4 |
| 35 | 0.7 | 3.5 |
| 36 | 1.1 | 4.4 |
| 37 | 11.5 | 63.6 |
| 38 | 1.8 | 16.5 |
| 39 | 23.5 | 111.3 |
| 40 | 2.8 | 23.0 |
| 41 | 0.7 | 1.2 |
| 42 | 0.5 | 1.3 |
| 43 | 0.7 | 1.2 |
| 44 | 99.5 | 114.2 |

TABLE 1-continued

| Example No. | JAK3 IC$_{50}$ (nM) | BTK IC$_{50}$ (nM) |
|---|---|---|
| 45 | 32 | 205.8 |
| 46 | 56.8 | 269.1 |
| 47 | 13.0 | 52.2 |
| 48 | 13.8 | 73.4 |
| 49 | >400 | 30 |
| Tofacitinib | 1.1~3.3 | — |
| Ibrutinib | — | 0.5~2.7 |

*comparative example

What is claimed is:

1. A compound represented by Chemical Formula 1:

Chemical Formula 1

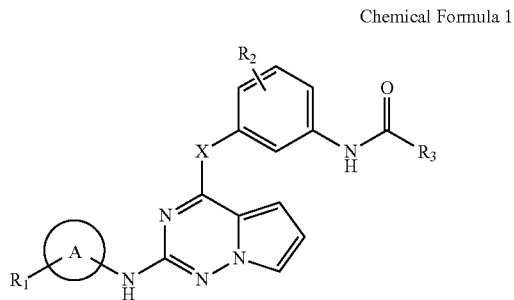

or a pharmaceutically acceptable salt or stereoisomer thereof,
wherein:
ring A is pyrrolyl, thiophenyl, pyrazolyl, isoxazolyl, isothiazolyl, thiazolyl, benzothiazolyl, or 4,5,6,7-tetrahydropyrazolo [1,5-a]pyrazinyl;
$R_1$ is H, $C_{1-4}$ alkyl, $C_{1-4}$ haloalkyl, C(O)phenyl, N($C_{1-4}$ alkyl)$_2$, O$C_{1-4}$ alkyl, $C_{3-6}$ cycloalkyl, or pyrazolyl, wherein the $C_{1-4}$ alkyl is optionally substituted with 1 substituent selected from the group consisting of CN, C(O)NH$C_{1-4}$ alkyl, N($C_{1-4}$ alkyl)$_2$, and O$C_{1-4}$ alkyl, and further wherein the pyrazolyl is optionally substituted with 1 or 2 independently selected $C_{1-4}$ alkyl substituents; or
$R_1$ is

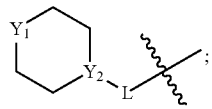

$R_2$ is H, halogen, or $C_{1-4}$ alkyl;
$R_3$ is $C_{1-4}$ alkyl, $C_{2-4}$ alkenyl, or $C_{2-4}$ alkynyl, wherein the $C_{1-4}$ alkyl is optionally substituted with 1 substituent selected from the group consisting of halogen and CN, and further wherein the $C_{2-4}$ alkenyl is optionally substituted with 1 halogen substituent;
L is a bond, —$C_{1-4}$ alkylene-, or —C(O)—;
X is —NH— or —O—;
$Y_1$ is —NH—, —N($C_{1-4}$ alkyl)-, or —O—; and
$Y_2$ is CH or N.

2. The compound according to claim 1, or a pharmaceutically acceptable salt or stereoisomer thereof, wherein $R_1$ is H, CH$_3$, CHF$_2$, CH$_2$CN, CH$_2$C(O)NHCH$_3$, CH$_2$N(CH$_3$)$_2$, CH$_2$CH$_3$, CH$_2$CHF$_2$, CH$_2$CF$_3$, CH$_2$CH$_2$N(CH$_2$CH$_3$)$_2$, CHN(CH$_2$CH$_3$)$_2$CH$_3$, CH$_2$CH$_2$OCH$_3$, CH(OCH$_3$)CH$_3$, CH$_2$CH$_2$CH$_3$, CH(CH$_3$)$_2$, CH$_2$CH$_2$CH$_2$CH$_3$, CH$_2$CH(CH$_3$)$_2$, C(O)phenyl, N(CH$_3$)$_2$, OCH$_3$, cyclopropyl, or 3,5-dimethyl-1H-pyrazol-1-yl.

3. The compound according to claim 1, or a pharmaceutically acceptable salt or stereoisomer thereof, wherein $R_1$ is:

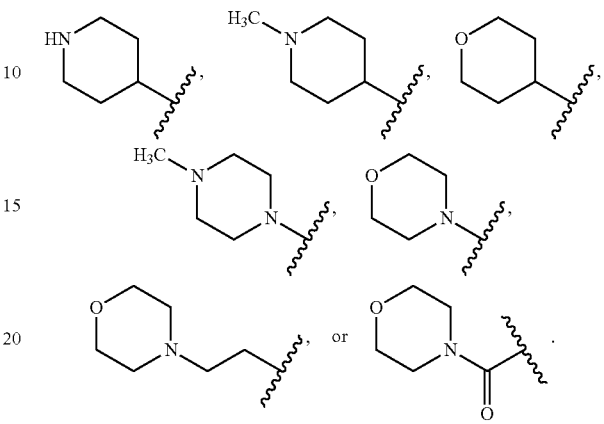

4. The compound according to claim 1, or a pharmaceutically acceptable salt or stereoisomer thereof, wherein $R_2$ is H, F, Cl, or CH$_3$.

5. The compound according to claim 1, or a pharmaceutically acceptable salt or stereoisomer thereof, wherein $R_3$ is CH$_2$Cl, CH=CH$_2$, CH=CHCH$_2$Cl, CH=CHCH$_2$CH$_3$, or C≡CCH$_2$CH$_3$.

6. The compound according to claim 1, or a stereoisomer thereof, wherein the compound, or stereoisomer thereof, is selected from the group consisting of:

1) N-(3-((2-((1-cyclopropyl-1H-pyrazol-4-yl)amino)pyrrolo[2,1-f][1,2,4]triazin-4-yl)oxy)-4-fluorophenyl) acrylamide,
3) N-(3-((2-((1-methyl-1H-pyrazol-4-yl)amino)pyrrolo[2,1-f][1,2,4]triazin-4-yl)oxy)phenyl)acrylamide,
4) N-(3-((2-((1-(2,2-difluoroethyl)-1H-pyrazol-4-yl)amino)pyrrolo[2,1-f][1,2,4]triazin-4-yl)oxy)phenyl) acrylamide,
5) N-(3-((2-((3-methylisothiazol-5-yl)amino)pyrrolo[2,1-f][1,2,4]triazin-4-yl)oxy)phenyl)acrylamide,
6) N-(3-((2-((1-ethyl-1H-pyrazol-4-yl)amino)pyrrolo[2,1-f][1,2,4]triazin-4-yl)oxy)phenyl)acrylamide,
7) N-(4-fluoro-3-((2-((3-methylisothiazol-5-yl)amino) pyrrolo[2,1-f][1,2,4]triazin-4-yl)oxy)phenyl)acrylamide,
8) N-(3-((2-((1-ethyl-1H-pyrazol-4-yl)amino)pyrrolo[2,1-f][1,2,4]triazin-4-yl)oxy)-4-fluorophenyl)acrylamide,
9) N-(4-fluoro-3-((2-((1-methyl-1H-pyrrol-3-yl)amino) pyrrolo[2,1-f][1,2,4]triazin-4-yl)oxy)phenyl)acrylamide,
10) N-(4-fluoro-3-((2-((1-isobutyl-1H-pyrazol-4-yl) amino)pyrrolo[2,1-f][1,2,4]triazin-4-yl)oxy)phenyl) acrylamide,
11) N-(3-((2-((1-cyclopropyl-1H-pyrazol-4-yl)amino) pyrrolo[2,1-f][1,2,4]triazin-4-yl)oxy)phenyl)acrylamide,
14) N-(3-((2-((benzo[d]thiazol-6-yl)amino)pyrrolo[2,1-f][1,2,4]triazin-4-yl)oxy)-4-fluorophenyl)acrylamide,
19) N-(3-((2-((thiophen-3-yl)amino)pyrrolo[2,1-f][1,2,4] triazin-4-yl)oxy)phenyl)acrylamide, 20) N-(3-((2-((1-methyl-1H-pyrazol-3-yl)amino)pyrrolo[2,1-f][1,2,4]triazin-4-yl)oxy)phenyl)acrylamide,
24) N-(3-((2-((5-methyl-4,5,6,7-tetrahydropyrazolo[1,5-a]pyrazin-2-yl)amino)pyrrolo[2,1-f][1,2,4]triazin-4-yl)oxy)phenyl)acrylamide,
26) N-(3-((2-((1-(2,2-difluoroethyl)-1H-pyrazol-4-yl)amino)pyrrolo[2,1-f][1,2,4]triazin-4-yl)oxy)-4-fluorophenyl)acrylamide,
27) N-(4-fluoro-3-((2-((1-methyl-1H-pyrazol-4-yl)amino)pyrrolo[2,1-f][1,2,4]triazin-4-yl)oxy)phenyl)acrylamide,
30) N-(4-fluoro-3-((2-((thiophen-3-yl)amino)pyrrolo[2,1-f][1,2,4]triazin-4-yl)oxy)phenyl)acrylamide,
32) N-(4-fluoro-3-((2-((1-propyl-1H-pyrazol-4-yl)amino)pyrrolo[2,1-f][1,2,4]triazin-4-yl)oxy)phenyl)acrylamide,
33) N-(3-((2-((1-(difluoromethyl)-1H-pyrazol-4-yl)amino)pyrrolo[2,1-f][1,2,4]triazin-4-yl)oxy)-4-fluorophenyl)acrylamide,
34) N-(4-fluoro-3-((2-((1-(tetrahydro-2H-pyran-4-yl)-1H-pyrazol-4-yl)amino)pyrrolo[2,1-f][1,2,4]triazin-4-yl)oxy)phenyl)acrylamide,
35) N-(4-fluoro-3-((2-((1-(2-morpholinoethyl)-1H-pyrazol-4-yl)amino)pyrrolo[2,1-f][1,2,4]triazin-4-yl)oxy)phenyl)acrylamide,
36) N-(4-fluoro-3-((2-((1-isopropyl-1H-pyrazol-4-yl)amino)pyrrolo[2,1-f][1,2,4]triazin-4-yl)oxy)phenyl)acrylamide,
37) N-(4-fluoro-3-((2-((1-(piperidin-4-yl)-1H-pyrazol-4-yl)amino)pyrrolo[2,1-f][1,2,4]triazin-4-yl)oxy)phenyl)acrylamide,
38) N-(4-fluoro-3-((2-((1-(2,2,2-trifluoroethyl)-1H-pyrazol-4-yl)amino)pyrrolo[2,1-f][1,2,4]triazin-4-yl)oxy)phenyl)acrylamide,
40) N-(4-fluoro-3-((2-((1-(2-methoxyethyl)-1H-pyrazol-4-yl)amino)pyrrolo[2,1-f][1,2,4]triazin-4-yl)oxy)phenyl)acrylamide,
41) 2-chloro-N-(3-((2-((1-(2,2-difluoroethyl)-1H-pyrazol-4-yl)amino)pyrrolo[2,1-f][1,2,4]triazin-4-yl)oxy)-4-fluorophenyl)acetamide,
42) 2-chloro-N-(4-fluoro-3-((2-((1-(tetrahydro-2H-pyran-4-yl)-1H-pyrazol-4-yl)amino)pyrrolo[2,1-f][1,2,4]triazin-4-yl)oxy)phenyl)acetamide,
43) 2-chloro-N-(3-((2-((1-ethyl-1H-pyrazol-4-yl)amino)pyrrolo[2,1-f][1,2,4]triazin-4-yl)oxy)-4-fluorophenyl)acetamide,
44) (E)-4-chloro-N-(3-((2-((1-ethyl-1H-pyrazol-4-yl)amino)pyrrolo[2,1-f][1,2,4]triazin-4-yl)oxy)-4-fluorophenyl)but-2-enamide,
45) N-(4-fluoro-3-(2-(isoxazol-4-ylamino)pyrrolo[2,1-f][1,2,4]triazin-4-yloxy)phenyl)acrylamide,
46) N-(4-chloro-3-((2-((1-ethyl-1H-pyrazol-4-yl)amino)pyrrolo[2,1-f][1,2,4]triazin-4-yl)oxy)phenyl)acrylamide,
47) N-(5-((2-((1-ethyl-1H-pyrazol-4-yl)amino)pyrrolo[2,1-f][1,2,4]triazin-4-yl)oxy)-2-methylphenyl)acrylamide,
48) N-(5-((2-((1-(2,2-difluoroethyl)-1H-pyrazol-4-yl)amino)pyrrolo[2,1-f][1,2,4]triazin-4-yl)oxy)-2-methylphenyl)acrylamide, and
49) N-(3-((2-((1-(2,2-difluoroethyl)-1H-pyrazol-4-yl)amino)pyrrolo[2,1-f][1,2,4]triazin-4-yl)oxy)-4-fluorophenyl)pent-2-ynamide, or a pharmaceutically acceptable salt thereof.

7. A pharmaceutical composition comprising a pharmaceutically acceptable carrier, adjuvant, or diluent and the compound according to claim 1, or a pharmaceutically acceptable salt or stereoisomer thereof, as an active ingredient.

8. A compound represented by Chemical Formula 1:

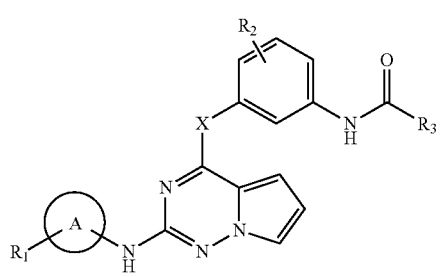

Chemical Formula 1 or a pharmaceutically acceptable salt or stereoisomer thereof,
wherein:
ring A is phenyl or pyridinyl;
$R_1$ is H, $C_{1-4}$ alkyl, $C_{1-4}$ haloalkyl, C(O)phenyl, N($C_{1-4}$ alkyl)$_2$, O$C_{1-4}$ alkyl, $C_{3-6}$ cycloalkyl, or pyrazolyl, wherein the $C_{1-4}$ alkyl is optionally substituted with 1 substituent selected from the group consisting of CN, C(O)NH$C_{1-4}$ alkyl, N($C_{1-4}$ alkyl)$_2$, and O$C_{1-4}$ alkyl, and further wherein the pyrazolyl is optionally substituted with 1 or 2 independently selected $C_{1-4}$ alkyl substituents; or
$R_1$ is

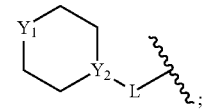

$R_2$ is halogen;
$R_3$ is $C_{1-4}$ alkyl, $C_{2-4}$ alkenyl, or $C_{2-4}$ alkynyl, wherein the $C_{1-4}$ alkyl is optionally substituted with 1 substituent selected from the group consisting of halogen and CN, and further wherein the $C_{2-4}$ alkenyl is optionally substituted with 1 halogen substituent;
L is a bond, —$C_{1-4}$ alkylene-, or —C(O)—;
X is —NH— or —O—;
$Y_1$ is —NH—, —N($C_{1-4}$ alkyl)-, or —O—; and
$Y_2$ is CH or N.

9. The compound according to claim 8, or a stereoisomer thereof, wherein the compound, or stereoisomer thereof, is selected from the group consisting of:
12) N-(3-((2-((4-(dimethylamino)phenyl)amino)pyrrolo[2,1-f][1,2,4]triazin-4-yl)oxy)-4-fluorophenyl)acrylamide,
13) N-(4-fluoro-3-((2-((4-phenoxyphenyl)amino)pyrrolo[2,1-f][1,2,4]triazin-4-yl)oxy)phenyl)acrylamide,
15) N-(4-fluoro-3-((2-((pyridin-3-yl)amino)pyrrolo[2,1-f][1,2,4]triazin-4-yl)oxy)phenyl)acrylamide,
25) N-(4-fluoro-3-((2-((4-(4-methylpiperazin-1-yl)phenyl)amino)pyrrolo[2,1-f][1,2,4]triazin-4-yl)oxy)phenyl)acrylamide,
28) N-(4-fluoro-3-((2-((4-methoxyphenyl)amino)pyrrolo[2,1-f][1,2,4]triazin-4-yl)oxy)phenyl)acrylamide,
29) N-(4-fluoro-3-((2-((4-(morpholine-4-carbonyl)phenyl)amino)pyrrolo[2,1-f][1,2,4]triazin-4-yl)oxy)phenyl)acrylamide, 31) N-(4-fluoro-3-((2-((4-morpholinophenyl)amino)pyrrolo[2,1-f][1,2,4]triazin-4-yl)oxy)phenyl)acrylamide, and
39) N-(3-((2-((4-(3,5-dimethyl-1H-pyrazol-1-yl)phenyl)amino)pyrrolo[2,1-f][1,2,4]triazin-4-yl)oxy)-4-fluorophenyl)acrylamide, or a pharmaceutically acceptable salt thereof.

\* \* \* \* \*